United States Patent
Kudo et al.

(10) Patent No.: US 9,572,710 B1
(45) Date of Patent: Feb. 21, 2017

(54) OCULAR IMPLANT INSERTION APPARATUS AND METHODS

(71) Applicant: Hoya Corporation, Tokyo (JP)

(72) Inventors: Kazunori Kudo, Saku (JP); Masahiro Noda, Toda (JP)

(73) Assignee: Hoya Corporation, Tokyo (JP)

( * ) Notice: Subject to any disclaimer, the term of this patent is extended or adjusted under 35 U.S.C. 154(b) by 0 days.

(21) Appl. No.: 15/336,678

(22) Filed: Oct. 27, 2016

Related U.S. Application Data

(63) Continuation of application No. 15/071,880, filed on Mar. 16, 2016, which is a continuation of application No. 14/145,846, filed on Dec. 31, 2013, now Pat. No. 9,314,373, which is a continuation of application No. 13/699,708, filed as application No. PCT/JP2011/063747 on Jun. 8, 2011, now Pat. No. 8,647,382.

(30) Foreign Application Priority Data

Jun. 10, 2010 (JP) .................................. 2010-132952

(51) Int. Cl.
- A61F 2/16 (2006.01)
- A61F 9/00 (2006.01)
- A61F 2/14 (2006.01)

(52) U.S. Cl.
CPC ............. *A61F 9/0017* (2013.01); *A61F 2/148* (2013.01); *A61F 2/167* (2013.01); *A61F 2/1667* (2013.01); *A61F 9/0008* (2013.01); *A61F 2002/1681* (2013.01)

(58) Field of Classification Search
CPC ........ A61F 2/148; A61F 9/0008; A61F 2/167; A61F 2/1662
See application file for complete search history.

(56) References Cited

U.S. PATENT DOCUMENTS

| | | |
|---|---|---|
| 2,761,446 A | 9/1956 | Reed |
| 4,205,747 A | 6/1980 | Gilliam et al. |
| 4,269,307 A | 5/1981 | LaHaye |
| 4,423,809 A | 1/1984 | Mazzocco |

(Continued)

FOREIGN PATENT DOCUMENTS

| | | |
|---|---|---|
| DE | 3610925 | 10/1987 |
| DE | 4110278 | 10/1992 |

(Continued)

OTHER PUBLICATIONS

U.S. Appl. No. 15/126,277, filed Sep. 14, 2016.

*Primary Examiner* — Todd J Scherbel
*Assistant Examiner* — Son Dang
(74) *Attorney, Agent, or Firm* — Henricks, Slavin & Holmes LLP

(57) ABSTRACT

An exemplary ocular implant insertion system includes a case and a preloaded ocular implant insertion apparatus. The apparatus includes first and second movable structures that move the ocular implant in a predetermined sequence. The respective configurations of the case and the ocular implant insertion apparatus are such that the ocular implant insertion apparatus is not removable from the case when the ocular implant insertion apparatus is in the pre-use state and is removable after the first movable structure has moved at least a portion of the optical implant.

11 Claims, 12 Drawing Sheets

(56) References Cited

U.S. PATENT DOCUMENTS

| | | |
|---|---|---|
| 4,573,998 A | 3/1986 | Mazzocco |
| 4,608,049 A | 8/1986 | Kelman |
| 4,634,423 A | 1/1987 | Bailey |
| 4,681,102 A | 7/1987 | Bartell |
| 4,697,697 A | 10/1987 | Graham et al. |
| 4,699,140 A | 10/1987 | Holmes |
| 4,702,244 A | 10/1987 | Mazzocco |
| 4,715,373 A | 12/1987 | Mazzocco et al. |
| 4,747,404 A | 5/1988 | Jampel et al. |
| 4,750,498 A | 6/1988 | Graham |
| 4,759,359 A | 7/1988 | Willis et al. |
| 4,763,650 A | 8/1988 | Hauser |
| 4,765,329 A | 8/1988 | Cumming et al. |
| 4,769,034 A | 9/1988 | Poley |
| 4,781,719 A | 11/1988 | Kelman |
| 4,787,904 A | 11/1988 | Severin |
| 4,810,249 A | 3/1989 | Haber et al. |
| 4,819,631 A | 4/1989 | Poley |
| 4,834,094 A | 5/1989 | Patton |
| 4,836,201 A | 6/1989 | Patton |
| 4,862,885 A | 9/1989 | Cumming |
| 4,880,000 A | 11/1989 | Holmes et al. |
| 4,919,130 A | 4/1990 | Stoy et al. |
| 4,934,363 A | 6/1990 | Smith et al. |
| 4,955,889 A | 9/1990 | Van Gent |
| 4,976,716 A | 12/1990 | Cumming |
| 4,988,352 A | 1/1991 | Poley |
| 4,994,028 A | 2/1991 | Leonard et al. |
| 5,066,297 A | 11/1991 | Cumming |
| 5,098,439 A | 3/1992 | Hill et al. |
| 5,123,905 A | 6/1992 | Kelman |
| 5,139,501 A | 8/1992 | Klaas |
| 5,171,241 A | 12/1992 | Buboltz et al. |
| 5,176,686 A | 1/1993 | Poley |
| 5,190,552 A | 3/1993 | Kelman |
| 5,190,553 A | 3/1993 | Kanert et al. |
| 5,222,972 A | 6/1993 | Hill et al. |
| 5,242,450 A | 9/1993 | McDonald |
| 5,259,395 A | 11/1993 | Li |
| 5,275,604 A | 1/1994 | Rheinish et al. |
| 5,281,227 A | 1/1994 | Sussman |
| 5,304,182 A | 4/1994 | Rheinish et al. |
| 5,354,333 A | 10/1994 | Kammann et al. |
| 5,395,378 A | 3/1995 | McDonald |
| 5,425,734 A | 6/1995 | Blake |
| 5,454,818 A | 10/1995 | Hambleton et al. |
| 5,468,246 A | 11/1995 | Blake |
| 5,474,562 A | 12/1995 | Orchowski et al. |
| 5,494,484 A | 2/1996 | Feingold |
| 5,496,328 A | 3/1996 | Nakajima et al. |
| 5,499,987 A | 3/1996 | Feingold |
| 5,562,676 A | 10/1996 | Brady et al. |
| 5,571,113 A | 11/1996 | McDonald |
| 5,578,042 A | 11/1996 | Cumming |
| 5,582,613 A | 12/1996 | Brady |
| 5,582,614 A | 12/1996 | Feingold |
| 5,584,304 A | 12/1996 | Brady |
| 5,616,148 A | 4/1997 | Eagles et al. |
| 5,620,450 A | 4/1997 | Eagles et al. |
| 5,643,275 A | 7/1997 | Blake |
| 5,643,276 A | 7/1997 | Zaleski |
| 5,645,534 A | 7/1997 | Chanoch |
| 5,653,715 A | 8/1997 | Reich et al. |
| 5,653,753 A | 8/1997 | Brady et al. |
| 5,702,402 A | 12/1997 | Brady |
| 5,702,441 A | 12/1997 | Zhou |
| 5,716,364 A | 2/1998 | Makker et al. |
| 5,728,075 A | 3/1998 | Levander |
| 5,728,102 A | 3/1998 | Feingold et al. |
| 5,735,858 A | 4/1998 | Makker et al. |
| 5,766,181 A | 6/1998 | Chambers et al. |
| 5,772,666 A | 6/1998 | Feingold et al. |
| 5,772,667 A | 6/1998 | Blake |
| 5,776,138 A | 7/1998 | Vidal et al. |
| 5,800,442 A | 9/1998 | Wolf et al. |
| 5,803,925 A | 9/1998 | Yang et al. |
| 5,807,400 A | 9/1998 | Chambers et al. |
| 5,810,833 A | 9/1998 | Brady et al. |
| 5,810,834 A | 9/1998 | Heyman |
| 5,860,984 A | 1/1999 | Chambers et al. |
| 5,860,986 A | 1/1999 | Reich et al. |
| 5,868,751 A | 2/1999 | Feingold |
| 5,868,752 A | 2/1999 | Makker et al. |
| 5,873,879 A | 2/1999 | Figueroa et al. |
| 5,876,406 A | 3/1999 | Wolf et al. |
| 5,876,407 A | 3/1999 | Makker et al. |
| 5,876,440 A | 3/1999 | Feingold |
| 5,891,152 A | 4/1999 | Feingold |
| 5,902,307 A | 5/1999 | Feingold et al. |
| 5,919,197 A | 7/1999 | McDonald |
| 5,921,989 A | 7/1999 | Deacon et al. |
| 5,928,245 A | 7/1999 | Wolf et al. |
| 5,941,886 A | 8/1999 | Feingold |
| 5,942,277 A | 8/1999 | Makker et al. |
| 5,944,725 A | 8/1999 | Cicenas |
| 5,947,974 A | 9/1999 | Brady et al. |
| 5,947,975 A | 9/1999 | Kikuchi et al. |
| 5,957,748 A | 9/1999 | Ichiha |
| 5,957,896 A | 9/1999 | Bendek et al. |
| 6,001,107 A | 12/1999 | Feingold |
| 6,010,510 A | 1/2000 | Brown et al. |
| 6,022,358 A | 2/2000 | Wolf et al. |
| 6,048,348 A | 4/2000 | Chambers et al. |
| 6,051,000 A | 4/2000 | Heyman |
| 6,056,757 A | 5/2000 | Feingold et al. |
| 6,056,758 A | 5/2000 | Vidal et al. |
| 6,059,791 A | 5/2000 | Chambers |
| 6,074,397 A | 6/2000 | Chambers et al. |
| 6,083,230 A | 7/2000 | Makker et al. |
| 6,093,193 A | 7/2000 | Makker et al. |
| 6,129,733 A | 10/2000 | Brady et al. |
| 6,142,999 A | 11/2000 | Brady et al. |
| 6,143,000 A | 11/2000 | Feingold |
| 6,162,229 A | 12/2000 | Feingold et al. |
| 6,174,315 B1 | 1/2001 | Chambers et al. |
| 6,214,015 B1 | 4/2001 | Reich et al. |
| 6,241,737 B1 | 6/2001 | Feingold |
| 6,248,111 B1 | 6/2001 | Glick et al. |
| 6,251,114 B1 | 6/2001 | Farmer et al. |
| 6,254,607 B1 | 7/2001 | Makker et al. |
| 6,267,768 B1 | 7/2001 | Deacon |
| 6,283,975 B1 | 9/2001 | Glick et al. |
| 6,283,976 B1 | 9/2001 | Portney |
| 6,312,433 B1 | 11/2001 | Butts |
| 6,334,862 B1 | 1/2002 | Vidal et al. |
| 6,336,932 B1 | 1/2002 | Figueroa et al. |
| 6,355,046 B2 | 3/2002 | Kikuchi et al. |
| 6,371,960 B2 | 4/2002 | Heyman et al. |
| 6,386,357 B1 | 5/2002 | Egawa |
| 6,387,101 B1 | 5/2002 | Butts et al. |
| 6,398,788 B1 | 6/2002 | Makker et al. |
| 6,406,481 B2 | 6/2002 | Feingold et al. |
| 6,428,545 B2 | 8/2002 | Portney |
| 6,447,519 B1 | 9/2002 | Brady et al. |
| 6,447,520 B1 | 9/2002 | Ott et al. |
| 6,468,282 B2 | 10/2002 | Kikuchi et al. |
| 6,471,708 B2 | 10/2002 | Green |
| 6,491,697 B1 | 12/2002 | Clark et al. |
| 6,497,708 B1 | 12/2002 | Cumming |
| 6,500,181 B1 | 12/2002 | Portney |
| 6,506,195 B2 | 1/2003 | Chambers et al. |
| 6,537,283 B2 | 3/2003 | Van Noy |
| 6,540,754 B2 | 4/2003 | Brady |
| 6,554,839 B2 | 4/2003 | Brady |
| 6,558,395 B2 | 5/2003 | Hjertman et al. |
| 6,605,093 B1 | 8/2003 | Blake |
| 6,607,537 B1 | 8/2003 | Binder |
| 6,629,979 B1 | 10/2003 | Feingold |
| 6,666,871 B2 | 12/2003 | Kikuchi et al. |
| 6,679,891 B2 | 1/2004 | Makker et al. |
| 6,685,740 B2 | 2/2004 | Figueroa et al. |
| 6,712,848 B1 | 3/2004 | Wolf et al. |
| 6,723,104 B2 | 4/2004 | Ott |
| 6,733,507 B2 | 5/2004 | McNicholas et al. |

(56) References Cited

U.S. PATENT DOCUMENTS

| | | | |
|---|---|---|---|
| 6,793,674 B2 | 9/2004 | Zapata |
| 6,858,033 B2 | 2/2005 | Kobayashi |
| 6,921,405 B2 | 7/2005 | Feingold et al. |
| 6,923,815 B2 | 8/2005 | Brady et al. |
| 6,976,989 B1 | 12/2005 | Vincent |
| 7,014,641 B2 | 3/2006 | Kobayashi et al. |
| 7,025,782 B2 | 4/2006 | Kobayashi et al. |
| 7,033,366 B2 | 4/2006 | Brady |
| 7,037,312 B2 | 5/2006 | Kikuchi et al. |
| 7,074,227 B2 | 7/2006 | Portney |
| 7,097,649 B2 | 8/2006 | Meyer |
| 7,131,976 B2 | 11/2006 | Kobayashi et al. |
| 7,156,854 B2 | 1/2007 | Brown et al. |
| 7,348,038 B2 | 3/2008 | Makker et al. |
| 7,422,604 B2 | 9/2008 | Vaquero et al. |
| 7,429,263 B2 | 9/2008 | Vaquero et al. |
| 7,458,976 B2 | 12/2008 | Peterson et al. |
| 7,476,230 B2 | 1/2009 | Ohno et al. |
| 7,494,505 B2 | 2/2009 | Kappelhof et al. |
| 7,645,300 B2 | 1/2010 | Tsai |
| 8,273,122 B2 | 9/2012 | Anderson |
| 8,382,769 B2 | 2/2013 | Inoue |
| 8,460,311 B2 | 6/2013 | Ishii |
| 8,470,032 B2 | 6/2013 | Inoue et al. |
| 8,475,528 B2 | 7/2013 | Ichinohe et al. |
| 8,523,877 B2 | 9/2013 | Ichinohe et al. |
| 8,523,941 B2 | 9/2013 | Ichinohe et al. |
| 8,535,375 B2 | 9/2013 | Ichinohe et al. |
| 8,545,512 B2 | 10/2013 | Ichinohe et al. |
| 8,574,239 B2 | 11/2013 | Ichinohe et al. |
| 8,603,103 B2 | 12/2013 | Kudo et al. |
| 8,647,382 B2 | 2/2014 | Kudo et al. |
| 8,702,795 B2 | 4/2014 | Shoji et al. |
| 8,747,465 B2 | 6/2014 | Someya et al. |
| 8,968,328 B2 | 3/2015 | Ichinohe et al. |
| 9,114,006 B2 | 8/2015 | Inoue |
| 9,114,007 B2 | 8/2015 | Ichinohe et al. |
| 9,186,246 B2 | 11/2015 | Inoue |
| 9,220,593 B2 | 12/2015 | Ichinohe |
| 9,289,288 B2 | 3/2016 | Someya et al. |
| 9,314,373 B2 | 4/2016 | Kudo et al. |
| 9,326,847 B2 | 5/2016 | Sanger |
| 9,364,320 B2 | 6/2016 | Ichinohe et al. |
| 2001/0007942 A1 | 7/2001 | Kikuchi et al. |
| 2002/0103490 A1 | 8/2002 | Brady |
| 2002/0151904 A1 | 10/2002 | Feingold et al. |
| 2002/0165610 A1 | 11/2002 | Waldock |
| 2002/0193805 A1 | 12/2002 | Ott et al. |
| 2003/0036765 A1 | 2/2003 | Van Noy |
| 2003/0040755 A1 | 2/2003 | Meyer |
| 2003/0050647 A1 | 3/2003 | Brady |
| 2003/0088253 A1 | 5/2003 | Seil |
| 2003/0139749 A1 | 7/2003 | Kikuchi et al. |
| 2003/0181921 A1 | 9/2003 | Jeannin |
| 2003/0195522 A1 | 10/2003 | McNicholas |
| 2003/0212406 A1 | 11/2003 | Kobayashi et al. |
| 2003/0212407 A1 | 11/2003 | Kikuchi |
| 2003/0212409 A1 | 11/2003 | Kobayashi et al. |
| 2004/0111094 A1 | 6/2004 | Meyer |
| 2004/0117012 A1 | 6/2004 | Vincent |
| 2004/0127911 A1 | 7/2004 | Figueroa |
| 2004/0186428 A1 | 9/2004 | Ray |
| 2004/0238392 A1 | 12/2004 | Peterson et al. |
| 2004/0243141 A1 | 12/2004 | Brown et al. |
| 2005/0033308 A1 | 2/2005 | Callahan et al. |
| 2005/0049605 A1 | 3/2005 | Vaquero et al. |
| 2005/0049606 A1 | 3/2005 | Vaquero et al. |
| 2005/0055011 A1 | 3/2005 | Enggaard |
| 2005/0125000 A1 | 6/2005 | Tourrette et al. |
| 2005/0143750 A1 | 6/2005 | Vaquero |
| 2005/0182419 A1 | 8/2005 | Tsai |
| 2005/0222578 A1 | 10/2005 | Vaquero |
| 2005/0261703 A1 | 11/2005 | Feingold et al. |
| 2006/0085013 A1 | 4/2006 | Dusek |
| 2006/0142781 A1 | 6/2006 | Pynson et al. |
| 2006/0167466 A1 | 7/2006 | Dusek |
| 2006/0200167 A1 | 9/2006 | Peterson et al. |
| 2006/0229633 A1 | 10/2006 | Shepherd |
| 2006/0235429 A1 | 10/2006 | Lee et al. |
| 2006/0293694 A1 | 12/2006 | Futamura |
| 2007/0005135 A1 | 1/2007 | Makker et al. |
| 2008/0033449 A1 | 2/2008 | Cole et al. |
| 2008/0058830 A1 | 3/2008 | Cole et al. |
| 2008/0086146 A1 | 4/2008 | Ishii et al. |
| 2008/0097459 A1 | 4/2008 | Kammerlander et al. |
| 2008/0221584 A1 | 9/2008 | Downer |
| 2009/0036898 A1 | 2/2009 | Ichinohe |
| 2009/0043313 A1 | 2/2009 | Ichinohe |
| 2009/0112223 A1 | 4/2009 | Downer et al. |
| 2009/0125034 A1 | 5/2009 | Pynson |
| 2009/0138022 A1 | 5/2009 | Tu et al. |
| 2009/0204122 A1 | 8/2009 | Ichinohe et al. |
| 2009/0216244 A1 | 8/2009 | Pynson |
| 2009/0248031 A1 | 10/2009 | Ichinohe |
| 2010/0094309 A1 | 4/2010 | Hboukhny et al. |
| 2010/0106160 A1 | 4/2010 | Tsai |
| 2010/0161049 A1 | 6/2010 | Inoue |
| 2010/0185206 A1 | 7/2010 | Ichinohe et al. |
| 2010/0217273 A1 | 8/2010 | Someya et al. |
| 2010/0286704 A1 | 11/2010 | Ichinohe et al. |
| 2010/0331808 A1 | 12/2010 | Py et al. |
| 2011/0082463 A1* | 4/2011 | Inoue .................. A61F 2/1664 606/107 |
| 2011/0098717 A1 | 4/2011 | Inoue |
| 2011/0264101 A1 | 10/2011 | Inoue et al. |
| 2011/0270264 A1 | 11/2011 | Shoji et al. |
| 2011/0288557 A1* | 11/2011 | Kudo et al. ............. A61F 2/167 606/107 |
| 2012/0022549 A1 | 1/2012 | Someya et al. |
| 2012/0071887 A1 | 3/2012 | Ichinohe et al. |
| 2013/0006259 A1 | 1/2013 | Sanger |
| 2013/0018460 A1 | 1/2013 | Anderson |
| 2013/0226193 A1 | 8/2013 | Kudo et al. |
| 2013/0245635 A1 | 9/2013 | Inoue |
| 2014/0081284 A1 | 3/2014 | Ichinohe et al. |
| 2014/0107660 A1 | 4/2014 | Ichinohe et al. |
| 2014/0114323 A1 | 4/2014 | Kudo et al. |
| 2014/0180299 A1 | 6/2014 | Ichinohe et al. |
| 2014/0180300 A1 | 6/2014 | Ichinohe et al. |
| 2014/0194890 A1 | 7/2014 | Kudo et al. |
| 2016/0113759 A1 | 4/2016 | Inoue |
| 2016/0193038 A1 | 7/2016 | Kudo et al. |

FOREIGN PATENT DOCUMENTS

| | | |
|---|---|---|
| EP | 0363213 | 4/1990 |
| EP | 0727966 | 9/2003 |
| EP | 1832247 A1 | 9/2007 |
| EP | 1338254 | 12/2008 |
| FR | 2749752 A | 12/1997 |
| JP | 63-197453 A | 8/1988 |
| JP | 4-212350 A | 8/1992 |
| JP | 5-103808 | 4/1993 |
| JP | 5-103809 | 4/1993 |
| JP | 8-024282 A | 1/1996 |
| JP | 8-505540 | 6/1996 |
| JP | 9-506285 A | 6/1997 |
| JP | 11-113939 A | 4/1999 |
| JP | 11-506357 A | 6/1999 |
| JP | 2000-516487 | 12/2000 |
| JP | 2000-516488 | 12/2000 |
| JP | 2001-502563 | 2/2001 |
| JP | 2001-104347 A | 4/2001 |
| JP | 2002-516709 A | 6/2002 |
| JP | 2002-355268 A | 12/2002 |
| JP | 2002-541912 A | 12/2002 |
| JP | 2003-144480 A | 5/2003 |
| JP | 3412106 B2 | 6/2003 |
| JP | 2003-210498 A | 7/2003 |
| JP | 2003-325569 A | 11/2003 |
| JP | 2003-325570 A | 11/2003 |
| JP | 2003-325572 A | 11/2003 |
| JP | 2004-024854 A | 1/2004 |
| JP | 2004-188194 A | 7/2004 |

(56) References Cited

FOREIGN PATENT DOCUMENTS

| | | |
|---|---|---|
| JP | 2004-351196 A | 12/2004 |
| JP | 2006-181269 A | 7/2006 |
| JP | 2006-297146 A | 11/2006 |
| JP | 2006-333924 A | 12/2006 |
| JP | 2006-333981 A | 12/2006 |
| JP | 2007-503872 A | 3/2007 |
| JP | 2007-152010 A | 6/2007 |
| JP | 2007-181604 A | 7/2007 |
| JP | 2007-526091 A | 9/2007 |
| JP | 2008-521535 A | 6/2008 |
| JP | 2008-212689 A | 9/2008 |
| JP | 2014-050484 A | 3/2014 |
| WO | WO9407436 A1 | 4/1994 |
| WO | WO9513022 A1 | 5/1995 |
| WO | WO9628122 A1 | 9/1996 |
| WO | WO9715253 A1 | 5/1997 |
| WO | WO9812969 A1 | 4/1998 |
| WO | WO9958086 A1 | 11/1999 |
| WO | WO9959668 A1 | 11/1999 |
| WO | WO0045746 A1 | 8/2000 |
| WO | WO0062712 A1 | 10/2000 |
| WO | WO2002071982 A1 | 9/2002 |
| WO | WO2002096322 A1 | 12/2002 |
| WO | WO2005023154 A1 | 3/2005 |
| WO | WO2005070341 A1 | 8/2005 |
| WO | WO2005084588 A1 | 9/2005 |
| WO | WO2006070628 A1 | 7/2006 |
| WO | WO2006080191 A1 | 8/2006 |
| WO | WO2006090531 A1 | 8/2006 |
| WO | WO2007037223 A1 | 4/2007 |
| WO | WO2007097221 A1 | 4/2007 |
| WO | WO2007080869 A1 | 7/2007 |
| WO | WO2008149794 A1 | 12/2008 |
| WO | WO2008149795 A1 | 12/2008 |
| WO | WO2009058929 A1 | 7/2009 |
| WO | WO2009148091 A1 | 12/2009 |
| WO | WO2011126144 A1 | 10/2011 |
| WO | WO2011155636 A1 | 12/2011 |

* cited by examiner

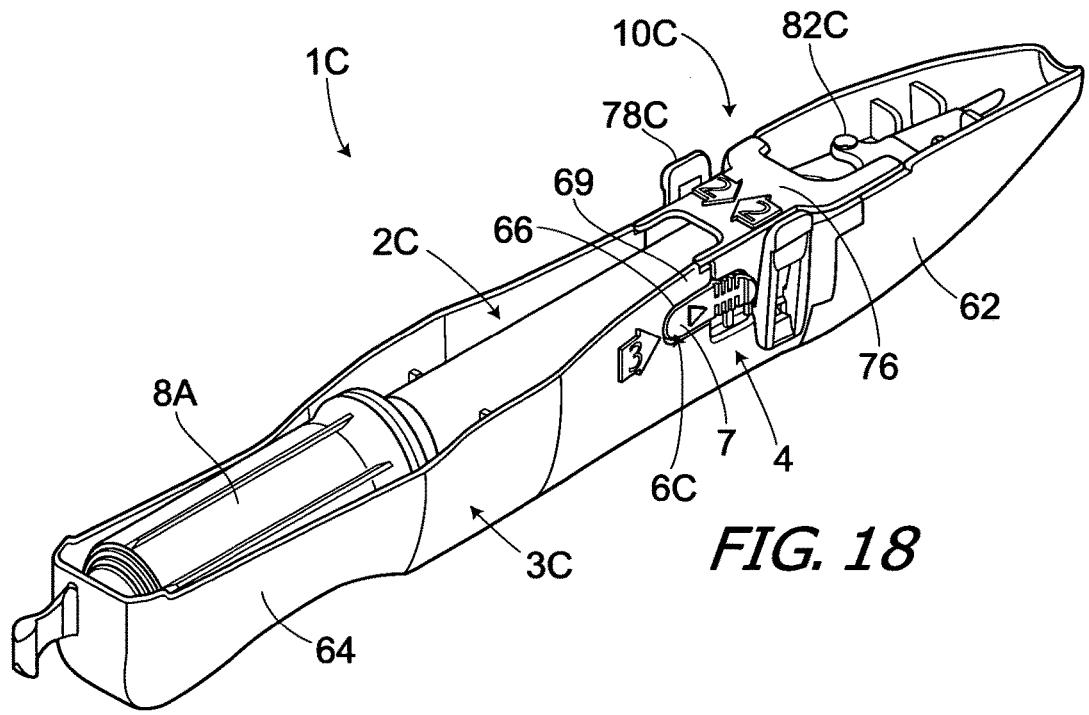
FIG. 18
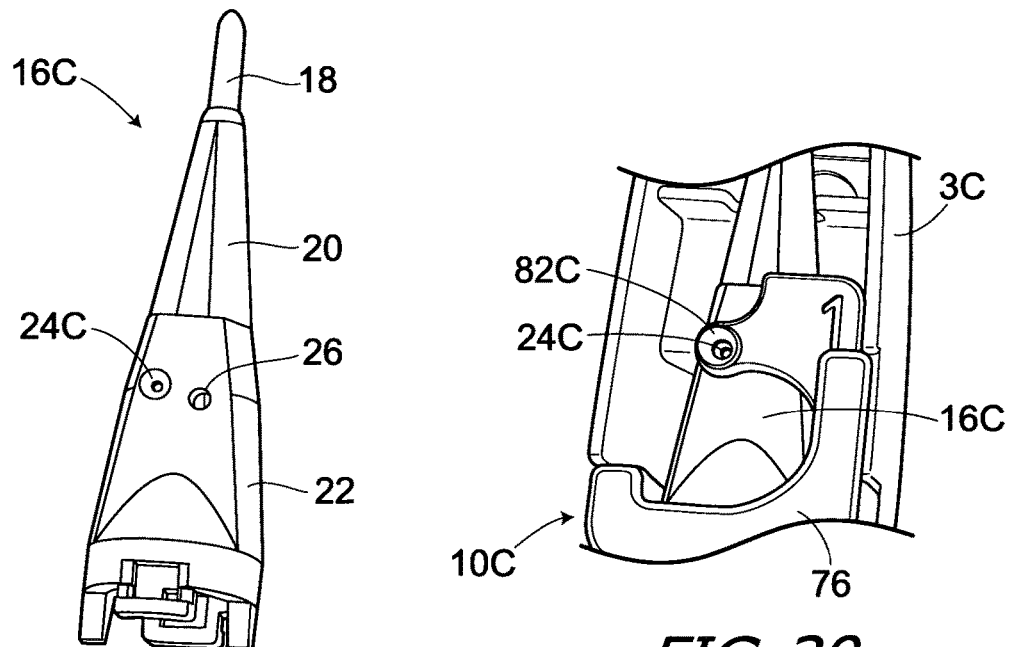
FIG. 19
FIG. 20

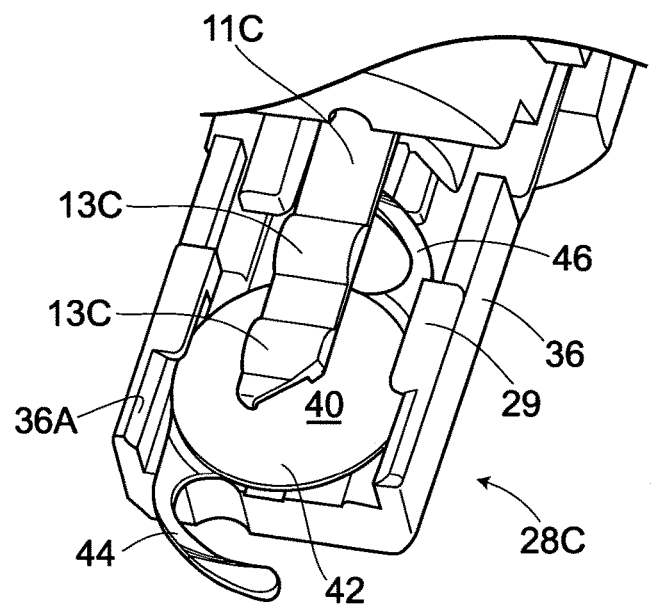
FIG. 21
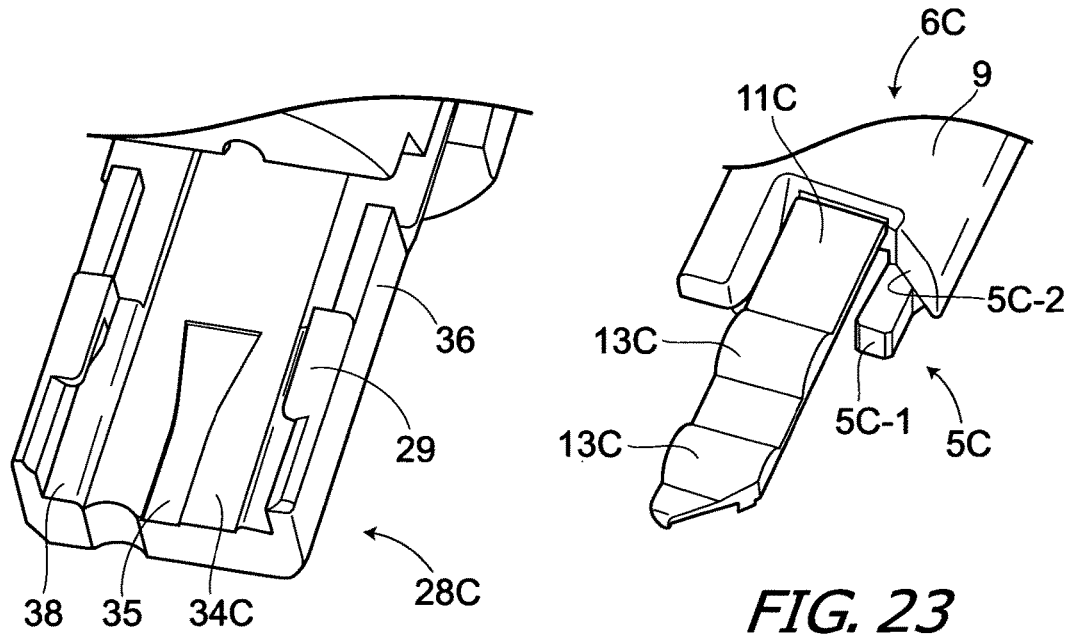
FIG. 22
FIG. 23

OCULAR IMPLANT INSERTION APPARATUS AND METHODS

CROSS-REFERENCE TO RELATED APPLICATIONS

This application is a continuation of U.S. application Ser. No. 15/071,880, filed Mar. 16, 2016, which is a continuation of U.S. application Ser. No. 14/145,846, filed Dec. 31, 2013, now U.S. Pat. No. 9,314,373, which is a continuation of U.S. application Ser. No. 13/699,708, now U.S. Pat. No. 8,647, 382, which has a 35 U.S.C. §371(c) date of May 11, 2013 and is a U.S. national phase application under 35 U.S.C. §371 of International Patent Application No. PCT/JP2011/ 063747, filed Jun. 8, 2011, which claims priority to Japanese patent application No. 2010-132952, filed Jun. 10, 2010. The International Application was published in English on Dec. 15, 2011 as International Publication No. WO 2011/155636 A1. The content of each application is incorporated herein in its entirety.

BACKGROUND OF THE INVENTIONS

1. Field of the Inventions

The present inventions relate generally to apparatus and methods for inserting an ocular implant into an eye.

2. Description of the Related Art

There are a variety of instances where an ocular implant is inserted into the anterior chamber, posterior chamber, cornea, vitreous space and/or other portion of an eye. Exemplary ocular implants include, but are not limited to, lenses, capsular tension rings, ocular prosthesis and lamellar transplants. An intraocular lens (IOL), for example, may be inserted into an aphakic eye that has undergone a cataract surgery or may be inserted into a phakic eye during a refractive surgery. One type of lens is a foldable lens. Foldable lenses are formed from soft material such as a silicone elastomer, soft acrylic, or hydrogel and may be inserted into the eye through a small incision. Lens insertion apparatus, which may be used to push a foldable lens into an eye through a nozzle, generally include screw-type insertion apparatus and push-type insertion apparatus. In both cases, the lens insertion apparatus may include a plunger that is used to push a folded lens through the nozzle into the eye by way of an incision that is relatively small, e.g., an incision that is smaller than the diameter of an IOL optic.

Loading an ocular implant into an inserter can be a troublesome portion of the insertion procedure. The implant may be contaminated, damaged or improperly placed into the inserter by operator, e.g., a surgeon or assistant. Accordingly, in some instances, the insertion apparatus is pre-loaded, i.e., the insertion apparatus is shipped from the factory with the ocular implant (e.g., an IOL) stored therein. An operator using a preloaded inserter does not place the implant into the insertion apparatus, thereby eliminating the possibility of the aforementioned operator error associated with loading.

In addition to the basic functions of storing and inserting an IOL or other ocular implant, it may also be desirable for the insertion apparatus to minimize the physical load on the ocular implant during storage in order to ensure that the ocular implant returns to its unstressed state after being inserted into the eye. It may also be desirable to fold the IOL or other ocular implant into as small a state as possible in order to reduce the size of the incision and the likelihood of corneal astigmatism caused by the surgery or infection. Thus, the desired insertion apparatus must be able to fold the unstressed ocular implant into a small state in a predetermined direction, and into a predetermined shape, in order to insure that the plunger can move the folded ocular implant through the nozzle without the insertion apparatus becoming clogged at or near the nozzle or the ocular implant being damaged. To that end, instead of using only a plunger to move the lens through the folding and insertion processes, some insertion apparatus have been configured to fold and move an IOL in stepwise fashion through the use of multiple IOL moving structures. Examples of such insertion apparatus are illustrated and described in PCT Pub. No. WO 2009/148091 (also published as US 2011/0082463) and Laid-open JP Pat. Pub. No. 2001-104347 (also published as US 2001/0007942).

The present inventor has, however, determined that insertion apparatus with multiple ocular implant moving structures are susceptible to improvement. For example, the present inventor has determined that such insertion apparatus are susceptible to erroneous operation, such as use of the moving structures in an incorrect sequence.

SUMMARY

An exemplary ocular implant insertion system includes a case and an ocular implant insertion apparatus including an ocular implant, a first movable structure that moves at least a portion of the ocular implant during movement thereof, and a second movable structure that moves the ocular implant through the nozzle. The ocular implant insertion apparatus is located at least partially within the case in pre-use state wherein the first and second movable structures have not folded and moved the ocular implant. The respective configurations of the case and the ocular implant insertion apparatus are such that the ocular implant insertion apparatus is not removable from the case when the ocular implant insertion apparatus is in the pre-use state and is removable after the first movable structure has moved at least a portion of the optical implant.

An exemplary method of using a system including a case and a preloaded ocular implant insertion apparatus locked to the case includes the steps of unlocking the insertion apparatus from the case by moving a first movable structure a distance sufficient to at least partial fold a stored ocular implant, removing the insertion apparatus from the case, and pushing the ocular implant from the insertion apparatus with a second movable structure.

There are a number of advantages associated with such systems and methods. For example, such systems and methods prevent the use of the first and second movable structures in an incorrect sequence.

BRIEF DESCRIPTION OF THE DRAWINGS

Detailed description of exemplary embodiments of the inventions will be made with reference to the accompanying drawings.

FIG. 18 is a perspective view of an IOL insertion system, including an IOL insertion apparatus and an insertion apparatus case, in accordance with one embodiment of a present invention.

FIG. 19 is a perspective view of the insertion tube of the exemplary IOL insertion apparatus illustrated in FIG. 18.

FIG. 20 is a perspective view of a portion of the exemplary IOL insertion system illustrated in FIG. 18.

FIG. 21 is a perspective view of a portion of the slider and the lens placement section of the exemplary IOL insertion apparatus illustrated in FIG. 18.

FIG. 22 is a perspective view of the lens placement section of the exemplary IOL insertion apparatus illustrated in FIG. 18.

FIG. 23 is a perspective view of a portion of the slider of the exemplary IOL insertion apparatus illustrated in FIG. 18.

DETAILED DESCRIPTION OF EXEMPLARY EMBODIMENTS

The following is a detailed description of the best presently known modes of carrying out the inventions. This description is not to be taken in a limiting sense, but is made merely for the purpose of illustrating the general principles of the inventions. The present inventions are also applicable to a wide variety of ocular implants which, as used herein, refers to any structure, instrumentality or device that is placed into any ocular structure or region. Ophthalmic lenses, capsular tension rings, ocular prosthesis and lamellar transplants are examples of ocular implants. Although the exemplary implementations are described below in the context of an intraocular lens (IOL), the present inventions are also applicable other types of ocular implants, including those yet to be developed. For example, the present inventions are applicable to other types of ophthalmic lenses. Such lenses include, but are not limited to, intraocular contact lenses, phakic IOLs, and other lenses that may be inserted into the eye.

I. OVERVIEW

Figure 1:
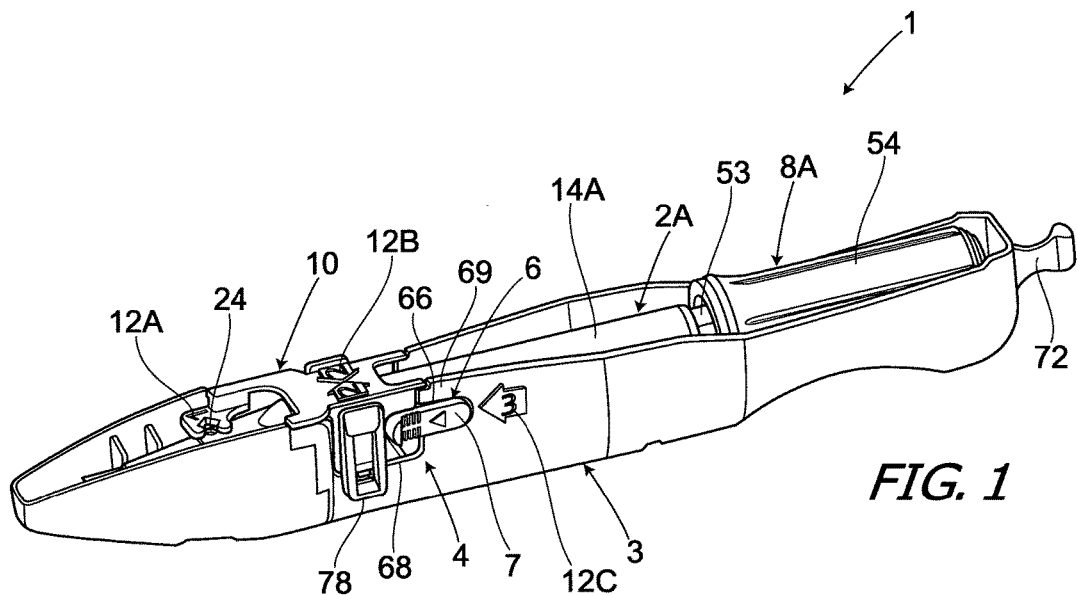
FIG. 1 is a perspective view of an IOL insertion system, including an IOL insertion apparatus and an insertion apparatus case, in accordance with one embodiment of a present invention.

As illustrated in FIG. 1, the exemplary IOL insertion system 1 includes an IOL insertion apparatus 2A and a case 3 in which the IOL insertion apparatus 2A is stored during shipping and at other times prior to an insertion procedure. The IOL insertion apparatus 2A is a preloaded insertion apparatus and, to that end, an IOL 40 (FIG. 5) is placed within the insertion apparatus during the assembly process and the insertion apparatus is shipped and stored with the IOL located therein. The IOL insertion system 1 includes a lock mechanism 4 that prevents the IOL insertion apparatus 2A from being removed from the case 3 when in a locked state, and allows the IOL insertion apparatus to be removed from the case when in an unlocked state. As is discussed in greater detail below, the operation of the IOL insertion apparatus 2A itself is, generally speaking, a two-step process where the steps must be performed in the proper sequence. The first step involves folding a previously unstressed IOL into a particular configuration with a first device and the second step pushing the folded IOL though a tapered passage, where it is further folded, and then into the eye. The IOL insertion system 1 is configured such that the lock mechanism 4 will transition from the locked state to the unlocked state, thereby allowing the IOL insertion apparatus 2A to be removed from the case 3, when the first step is performed. In other words, the IOL insertion system 1 is configured such that the operator will not be able to remove the IOL insertion apparatus 2A from the case 3 unless the first step in the process has been performed. By requiring the first step to be performed prior to removal of the IOL insertion apparatus 2A from the case 3, the IOL insertion system 1 forces the operator to perform the steps in the correct order.

II. EXEMPLARY IOL INSERTION APPARATUS

Figure 2:
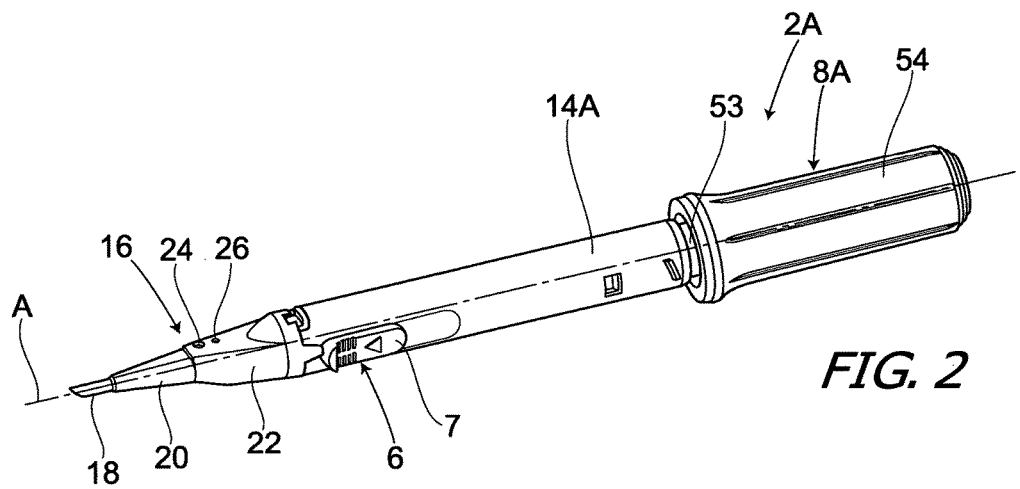
FIG. 2 is a perspective view of the exemplary IOL insertion apparatus illustrated in FIG. 1.

Turning to FIG. 2, the exemplary IOL insertion apparatus 2A includes a slider 6, a plunger 8A, a main body 14A and an insertion tube 16 that is mounted on the forward end of the main body. The main body 14A and insertion tube 16 together define the external housing of the insertion apparatus 2A. The slider 6 and plunger 8A are movable relative to the external housing and relative to each other.

Operation of the IOL insertion apparatus 2A, where the IOL is pushed out of the apparatus and into the eye, is referred to herein as a "push-out" or "insertion" process. The slider 6, which has a pair of finger grips 7, performs the first step in the insertion process, i.e., folding a previously unstressed IOL into a particular configuration, and may therefore be referred to as one example of a first lens push-out mechanism. The exemplary slider 6 pushes the IOL 40 distally as it folds the IOL. In other implementations, the first "push-out" mechanism may perform the first step of the "push-out" process by simply folding an IOL without moving it distally. The exemplary plunger 8A performs the second step in the insertion process, i.e., pushing the folded IOL through a tapered lumen and then into the eye, and may therefore be referred to as one example of a second lens push-out mechanism. The IOL moves along a lens advancement axis A during the insertion process. Movement of the movable components of the insertion apparatus 2A and the IOL 40 towards the eye is referred to herein as movement in the forward (or "distal") direction and movement away from the eye is referred to herein as movement in the rearward (or "proximal") direction. Similarly, the end of a structure that faces the eye during use is referred to as the forward (or "distal") end and the other end the structure is referred to as the rearward (or "proximal") end. The slider 6 and plunger 8A are both movable in the forward and rearward directions relative to the main body 14A.

Figure 3:
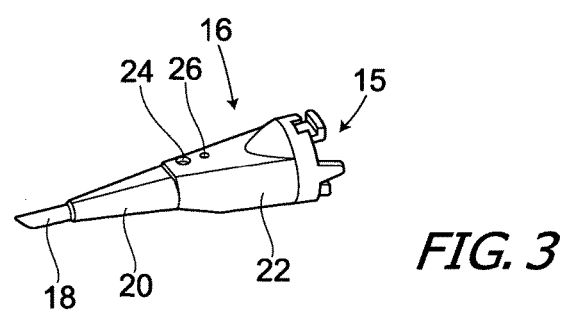
FIG. 3 is a perspective view of the insertion tube of the exemplary IOL insertion apparatus illustrated in FIG. 2.

The exemplary insertion tube 16 includes a nozzle 18, a transition section 20 and a protector 22, with interior regions that are in communication with one another so that an IOL can pass therethrough. The insertion tube 16 is connected to the main body 14A by a connector arrangement 15 (FIG. 3) on the insertion tube and a corresponding connector arrangement 17 (FIG. 4) on the main body. The inner diameter of the transition section 20 tapers downwardly from the end adjacent to the protector 22 to the end adjacent the nozzle 18. The protector 22 has an injection port 24 for viscoelastic material and a first insertion hole 26 (discussed below).

Figure 4:
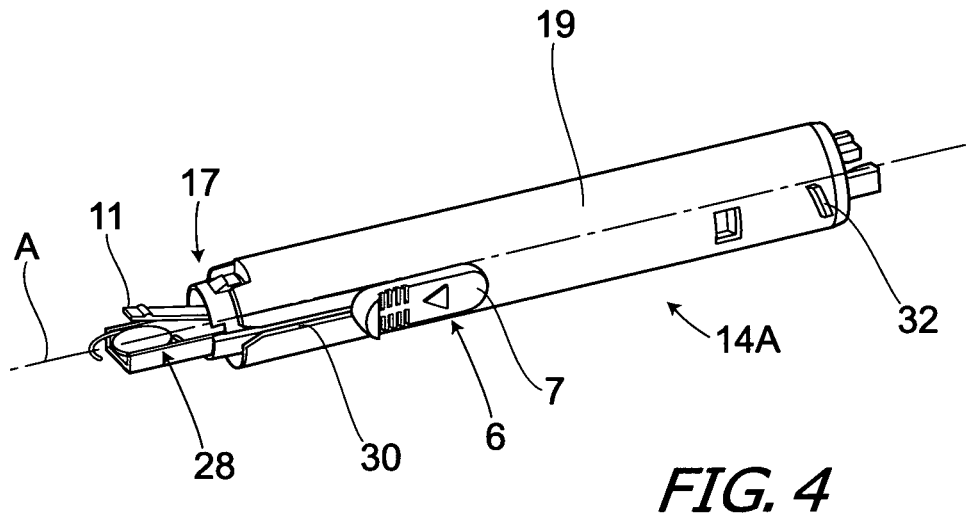
FIG. 4 is a perspective view of the main body of the exemplary IOL insertion apparatus illustrated in FIG. 2.

Turning to FIG. 4, the exemplary main body 14A includes a tubular member 19, a lens placement section 28, a slider guide section 30 and a protrusion 32. The lens placement section 28 (described below with reference to FIG. 5) protrudes distally from the front end of the tubular member 19. The slider guide section 30 is configured to allow the slider 6 to move forwardly and rearwardly. The slider guide section 30 may be a pair of slits, formed in the tubular member 19, that are parallel to the lens advancement axis A. The slider guide section 30 also extends rearwardly from the distal end of the tubular member 19 to the central portion of the tubular member. The plunger 8A is threadedly connected to the main body 14A in the illustrated implementation. To that end, the exemplary main body 14A includes a male screw. The protrusion 32, which is transverse to the lens advancement axis A, defines a portion of the screw thread of the male screw and a portion of the outer surface of the tubular member 19 defines the root of the thread. Another protrusion (not shown) may be located on the tubular member 19 180 degrees offset from the tubular member 32.

Figure 5:
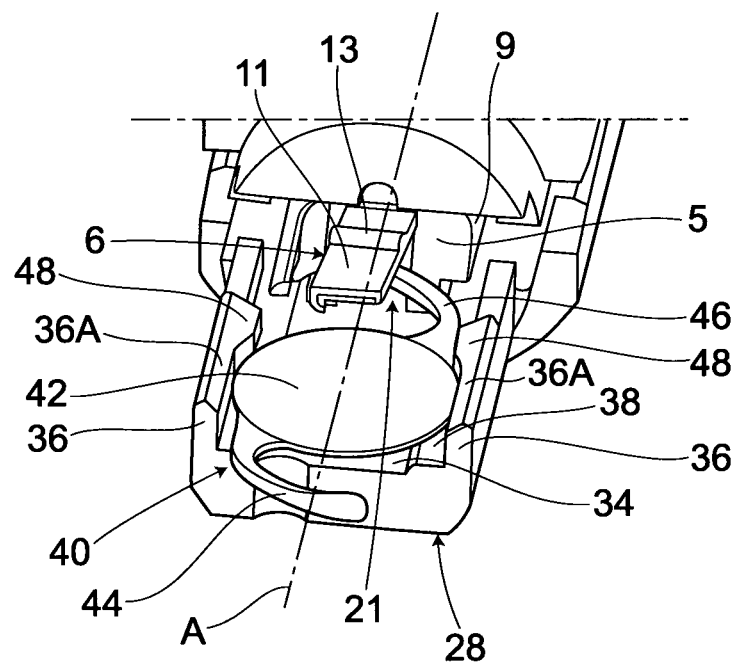
FIG. 5 is a perspective view of the lens placement section of the exemplary IOL insertion apparatus illustrated in FIG. 2.

As shown in FIG. 5, the IOL insertion apparatus 2A may be used to store an IOL 40 that has an optic 42 and a pair of supports 44 and 46 such as, for example, the illustrated pair of haptics. The exemplary lens placement section 28 includes a bottom surface 34, a pair of side walls 36 respectively located on opposite sides of the bottom surface and extending upwardly from the bottom surface, and a pair of rails 38. The bottom surface 34 and the side walls 36 are parallel to the lens advancement axis A and the lens advancement axis A is located between the side walls. The side walls 36 each include, near the upper end, an inclined surface 36A. The rear portions of the side walls 36 include inward protrusions 48 that prevent the IOL 40 from moving in the rearward direction. The lens supporting surfaces of the rails 38 are oriented in a direction that is transverse to the lens advancement axis A and slope away from the axis A in the rearward to forward direction. As such, the stored IOL 40 is tilted relative to the lens advancement axis A, with the forward end of the IOL optic 42 closer to the bottom surface 34 than the rearward end. The lens supporting surfaces of the rails 38 are also located a sufficient distance above the bottom surface 34 to prevent the IOL optic 42 from coming into contact with the bottom surface (note FIG. 6).

It should be noted that references herein to "top," "bottom," "upward," "downward" and the like are merely references to the illustrated orientation and/or the relationship of the components relative to one another in the illustrated orientation. For example, the side of the IOL 40 facing the bottom surface 34 is referred to "the downward side" and movement toward the bottom surface is referred to as movement in the "downward direction," while the opposite side of the IOL 40 is referred to as the "the upward side" and movement away from the bottom surface 34 is referred to as movement in the "the upward direction."

Figure 14:
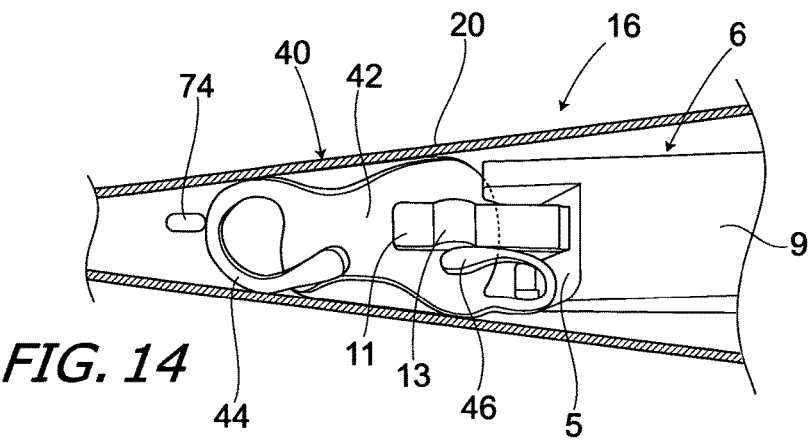
FIG. 14 is a partial section view showing another aspect of the operation of the exemplary IOL insertion system illustrated in FIG. 1.

In addition to the grips 7, and referring to FIGS. 5 and 14, the exemplary slider 6 includes an elongate member 9, with a lens contact surface 5, that is carried within the main body 14A and is slidable relative thereto. The grips 7 are connected to elongate member 9. The lens contact surface 5, which is larger than the plunger distal end 55 (discussed below), is used to scoop up the proximal IOL support 46 during the initial folding of the IOL 40. A lens holder 11 is pivotably mounted on the distal end of elongate member 9 and includes a protrusion 13. The lens holder 11 controls the initial folding of the IOL 40 during the first step of the lens insertion process. More specifically, as the slider 6 moves distally, the protrusion 13 rides along the tapered inner surface of the transition section 20, which causes the lens holder 11 to pivot downwardly into contact with the IOL optic 42 to fold the IOL 40. The slider elongate member 9 also includes a slot 21 through which the plunger rod 51 (discussed below) passes during the second step of the insertion process. Additional discussion concerning the use of a lens holder to fold an IOL may be found in, for example, U.S. Pat. Pub. No. 2010/0185206.

Figure 6:
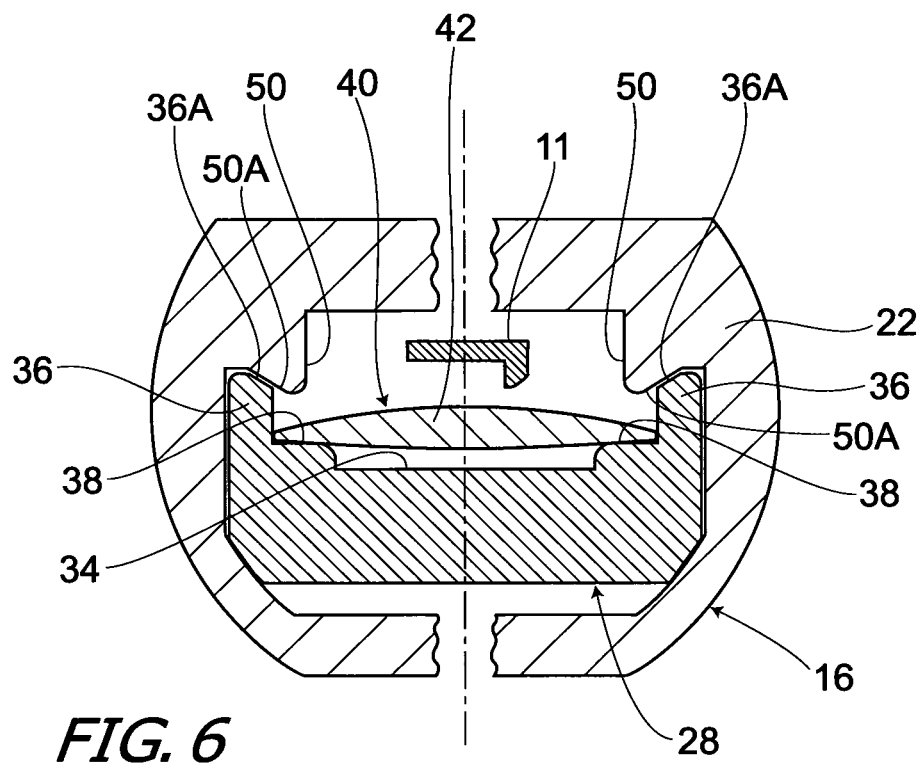
FIG. 6 is a section view of the insertion tube and lens placement section of the exemplary IOL insertion apparatus illustrated in FIG. 2.

Referring to FIG. 6, the protector 22 of exemplary insertion tube 16 includes protrusions 50, with inclined surfaces 50A, that extend downwardly and inwardly from both sides of the protector inner surface. The projections 50, which guide the insertion tube 16 onto the upper ends of the side walls 36 during assembly, are sized such that the inclined surfaces 50A extend beyond the side wall inclined surface 36A. This prevents the outer edge of the IOL optic 42 located in the lens placement section 28 from becoming wedged between the protrusions 50 and the side walls 36.

Figure 7:
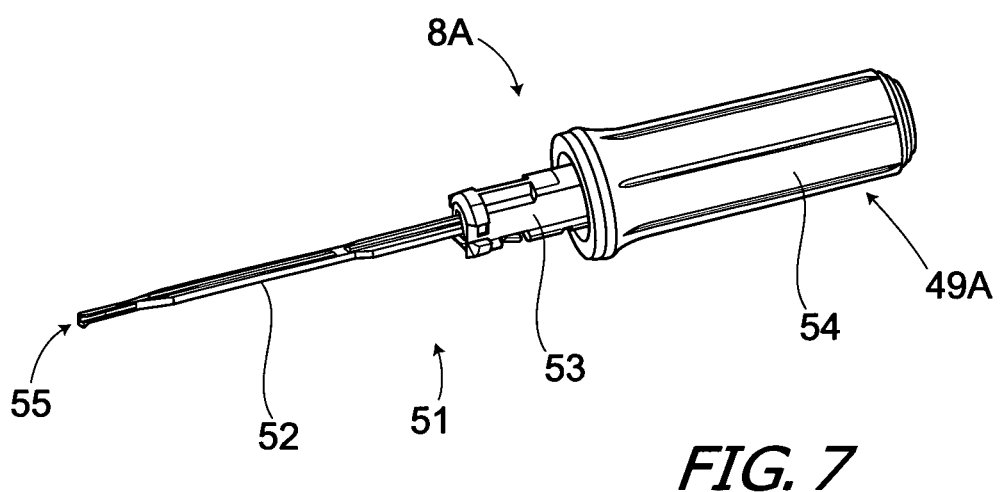
FIG. 7 is a perspective view of the plunger of the exemplary IOL insertion apparatus illustrated in FIG. 2.

Turning to FIG. 7, the exemplary plunger 8A includes an operational member 49A and a rod 51 with a distal rod portion 52, a proximal rod portion 53, and a rod distal end 55. The distal rod portion 52, which is sized such that it can be inserted through the nozzle 18, may be connected to, or may be integral with, the proximal rod portion 53. The operational portion 49A includes a handle 54 that is generally cylindrical in shape. The proximal (or "rearward") end of the handle 54 is rotatably journaled, or is otherwise rotatably secured, to the proximal (or "rearward") end of the proximal rod portion 53. The handle 54 is also hollow and configured to receive the proximal portion of the main body 14A. The inner surface of the handle 54 includes a female screw (not shown) with threads that operationally correspond to the threads on the male screw associated with the main body 14A (note protrusion 32 in FIG. 4). As such, after the plunger 8A has been moved distally from the position illustrated in FIG. 2 until the male thread defined in part by the protrusion 32 engages the female thread within the handle 54, further distal movement is accomplished by rotating the handle.

Figure 8:
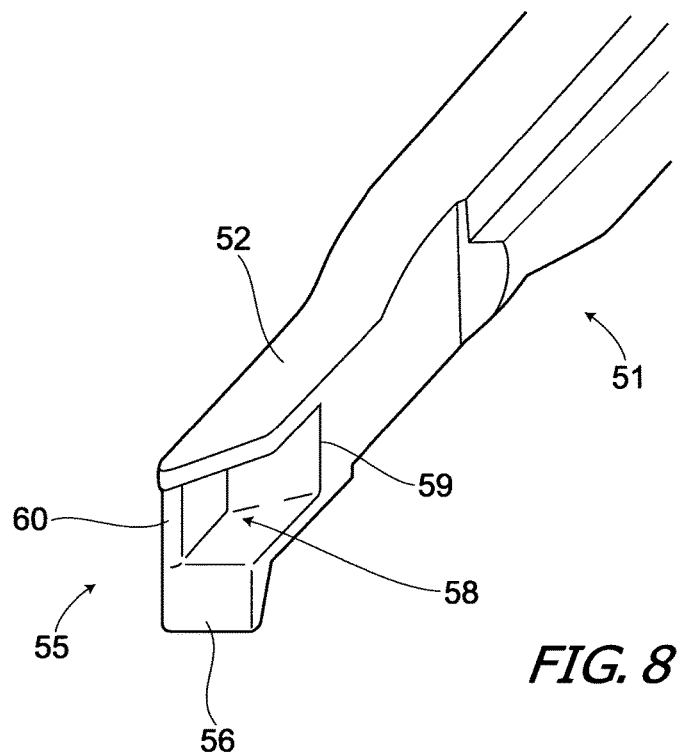
FIG. 8 is a perspective view of the distal portion of the plunger rod of the exemplary IOL insertion apparatus illustrated in FIG. 2.

As illustrated for example in FIG. 8, the rod distal end 55 may have a lens contact portion 56 and a recess 58 in which the free end of the proximal IOL support 46 is located during the second step of the two-step process. The exemplary lens contact portion 56 is a planar surface that is perpendicular to the lens advancement axis A, and is provided on a lower portion of the rod distal end 55. The exemplary recess 58, which has an opening 59 on one lateral side and a wall 60 on the other lateral side, is located above the lens contact portion 56. The recess 58 may be formed by cutting (or otherwise removing) material from the rod distal portion 52, starting at the distal end 55, or by molding the rod in the illustrated configuration. The wall 60 engages the outer edge of the IOL optic 42 and prevents optic of the folded IOL 40 from entering the recess 58. The wall 60 also keeps the IOL support 46 within the recess 58. The distal end of the wall 60 may be in the same plane as the lens contact portion 56 (as shown) or may be located distally beyond the lens contact portion 56.

With respect to operation of the exemplary IOL insertion apparatus 2A, and as alluded to above, the IOL 40 is initially pushed forwardly (or distally) and folded into a predetermined shape with the slider 6. The slider 6 also forms part of the lock mechanism 4 that locks the IOL insertion apparatus 2A to the case 3 and, as is discussed below, the initial forward movement of the slider, unlocks the lock mechanism. The folded IOL 40 is subsequently pushed by the plunger 8A forwardly (or distally) through the transition section 20 where it is further folded, then thorough the nozzle 18, and then into the eye. In other words, the exemplary IOL insertion apparatus 2A deforms an IOL that has been preloaded within the main body 14A and insertion tube 16 into a predetermined shape while moving the IOL in the forward direction, first by using the slider 6 and second by using the plunger 8A, and then discharges the folded IOL into the eye. The IOL 40 may be folded by operation of the slider 6 into the predetermined shape in which the optic 42 is curled up and around the lens advancement axis A, with an upper surface of the optic dented downwardly, and in which the free ends of the supports 44 and 46 are tucked into the upper surface of the curled optic 42 (note FIG. 14).

III. EXEMPLARY CASE

Figure 9:
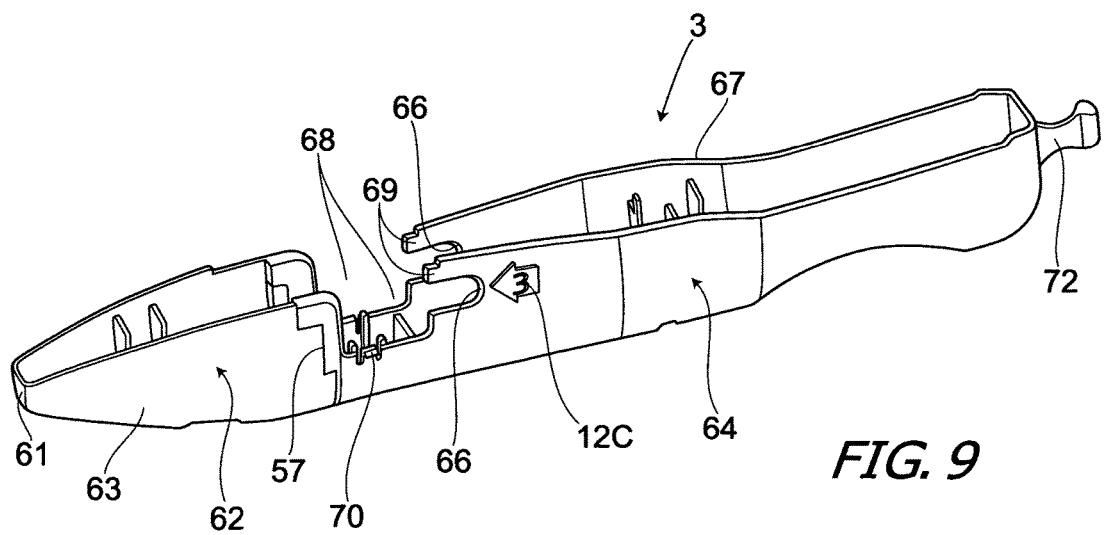
FIG. 9 is a perspective view of the exemplary insertion apparatus case illustrated in FIG. 1.

The case 3, which protects the IOL insertion apparatus 2A during shipping and storage, may be an elongated container with an open upper end. To that end, and referring to FIG. 9, the exemplary case 3 includes a pair of end walls 61, a pair of side walls 63 that each extend from one end wall to the other, and a bottom wall 65 (FIG. 10) at the bottom ends of the end and side walls. The top ends of the end walls 61 and side walls 63 define the open upper end 67 of the case 3. The front portion of the case 3 is identified by reference numeral 62 and the rear portion of the case is identified by referent numeral 64. The front and rear portions 62 and 64 may be separable structures that are secured to one another during the assembly process (note joint 57) as is discussed below.

The case 3 also includes a portion of the lock mechanism 4 that locks the IOL insertion apparatus 2A to the case. In the illustrated embodiment, each of the side walls 63 includes a storage slot 66 and removal slot 68. The storage slots 66 are separated, in the upward direction, from the open upper end 67 of the case by projections 69. The removal slots 68 extend to and through the upper end 67 of the case 3, and each storage slot 66 extends to the adjacent removal slot. Engagement members 70, which are located at the lower end of each removal slot 68, may be detachably engaged with a cover 10 (FIG. 1) to secure the cover to the case 3. A handle 72 may be located on the rear end wall 61 and used to remove the IOL insertion system 1 from the sterile package in which it is stored. The slider grips 7 are respectively located within the storage slots 66 when the lock mechanism 4 is in a locked state (FIG. 1) and are located within the removal slots when the lock mechanism is in an unlocked state (FIG. 13). The width of the slider grips 7 (in the direction of axis A) is less than or equal to the width of the removal slots 68. The respective configurations of the IOL insertion apparatus 2A and case 3 are also such that the slider grips 7 can be located within the storage slots 66 when the slider 6 is in its retracted, storage location (FIG. 12) and can also be pushed distally beyond the storage slots 66 to the point at which the slider 6 has completed the initial folding of the IOL 40 (FIG. 13).

Figure 12:
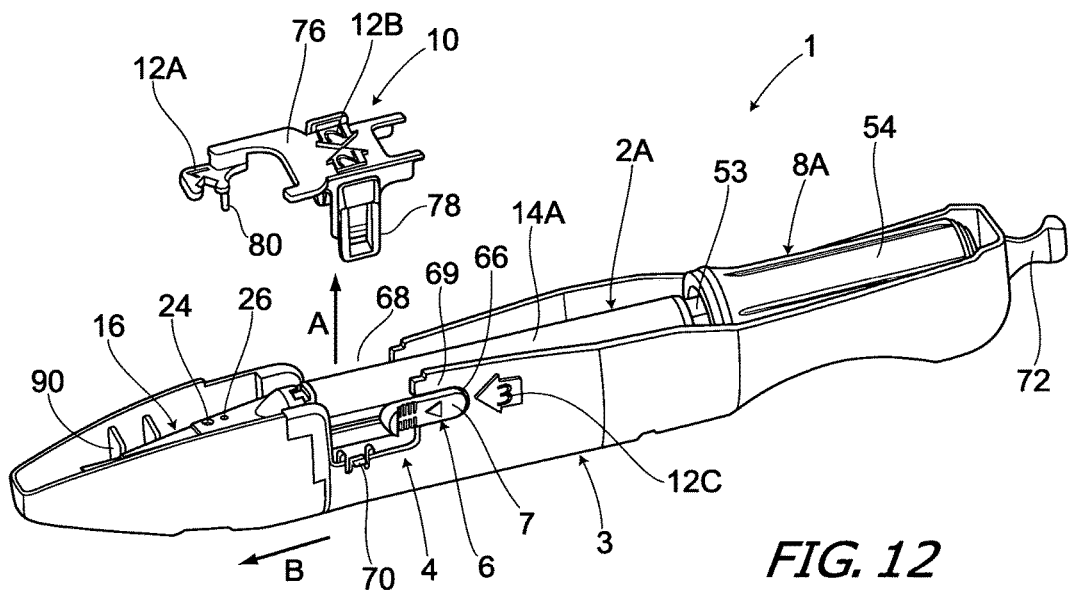
FIG. 12 is a perspective view showing one aspect of the operation of the exemplary IOL insertion system illustrated in FIG. 1.
Figure 13:
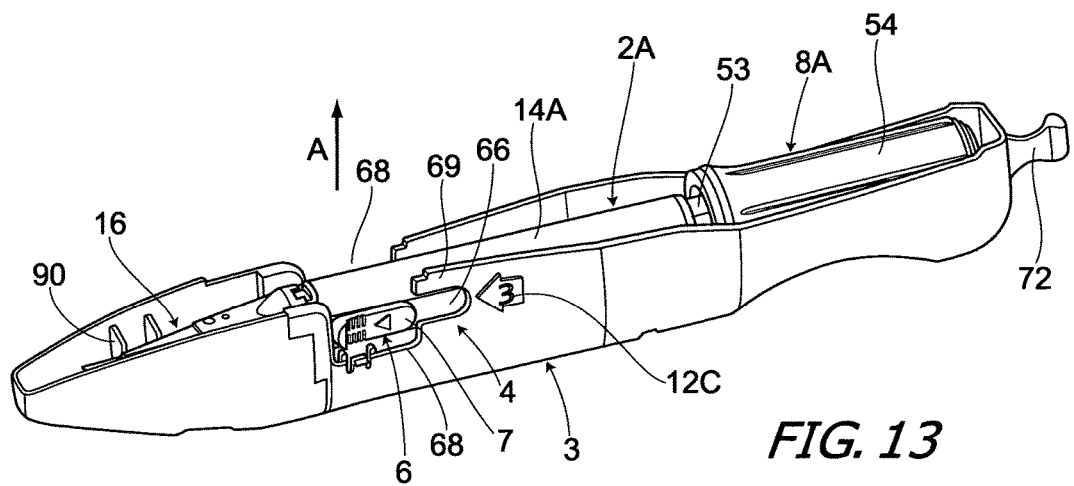
FIG. 13 is a perspective view showing another aspect of the operation of the exemplary IOL insertion system illustrated in FIG. 1.

With respect to the locked state, the projections 69 prevent the slider grips 7 and, therefore, the IOL insertion apparatus 2A, from moving in the upward direction identified by arrow A in FIGS. 12 and 13. The projections 69 do not, on the other hand, prevent the slider grips 7 from moving upwardly when the slider grips are located within the removal slots 68.

The exemplary case 3 also includes structure that helps control the initial folding of the lens during the movement of the slider 6 moves from the position illustrated in FIG. 12 to the position illustrated in FIG. 13. To that end, and referring to FIG. 10, the front portion 62 of the exemplary case 3 includes a protrusion 74 that extends through a correspondingly sized and located insertion hole 75 on the bottom surface of the insertion tube 16. The exemplary protrusion 74 has an overall ellipsoidal shape that is elongate in a direction parallel to the lens advancement axis A, and has a rearward facing surface that is slanted upwardly in the lens advancement (i.e., proximal to distal) direction. The protrusion 74 is located within the path of the IOL 40 and used to deflect the distal IOL support 44, as is discussed below with reference to FIG. 14. The protrusion 74 is removed from the IOL path, by way of the insertion hole 75, when the IOL insertion apparatus 2A is removed from the case 3.

Figure 10:
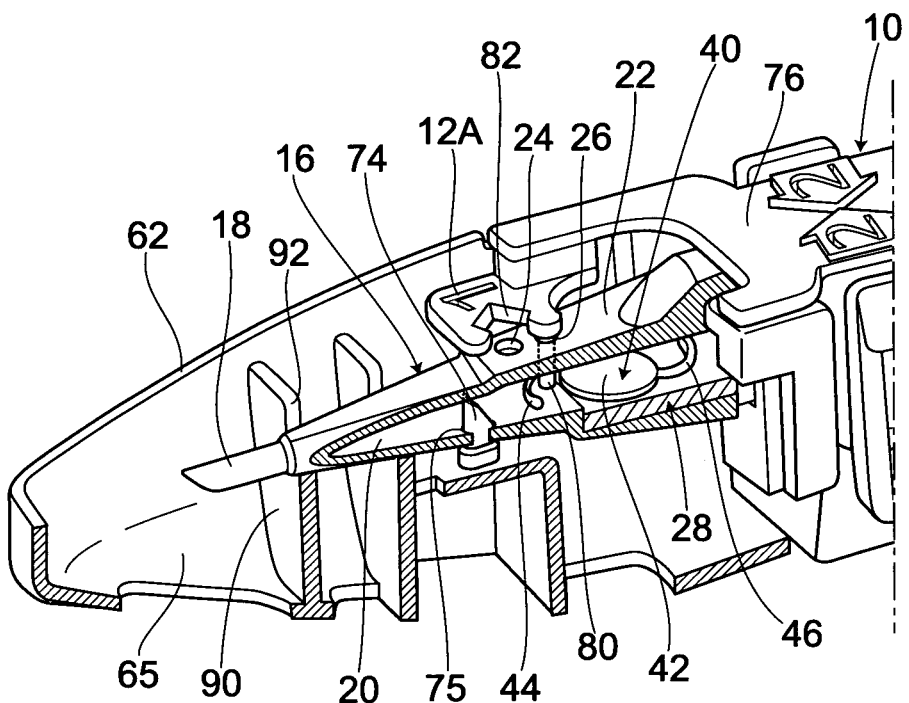
FIG. 10 is a partial section view of a portion of the exemplary IOL insertion system illustrated in FIG. 1.
Figure 15:
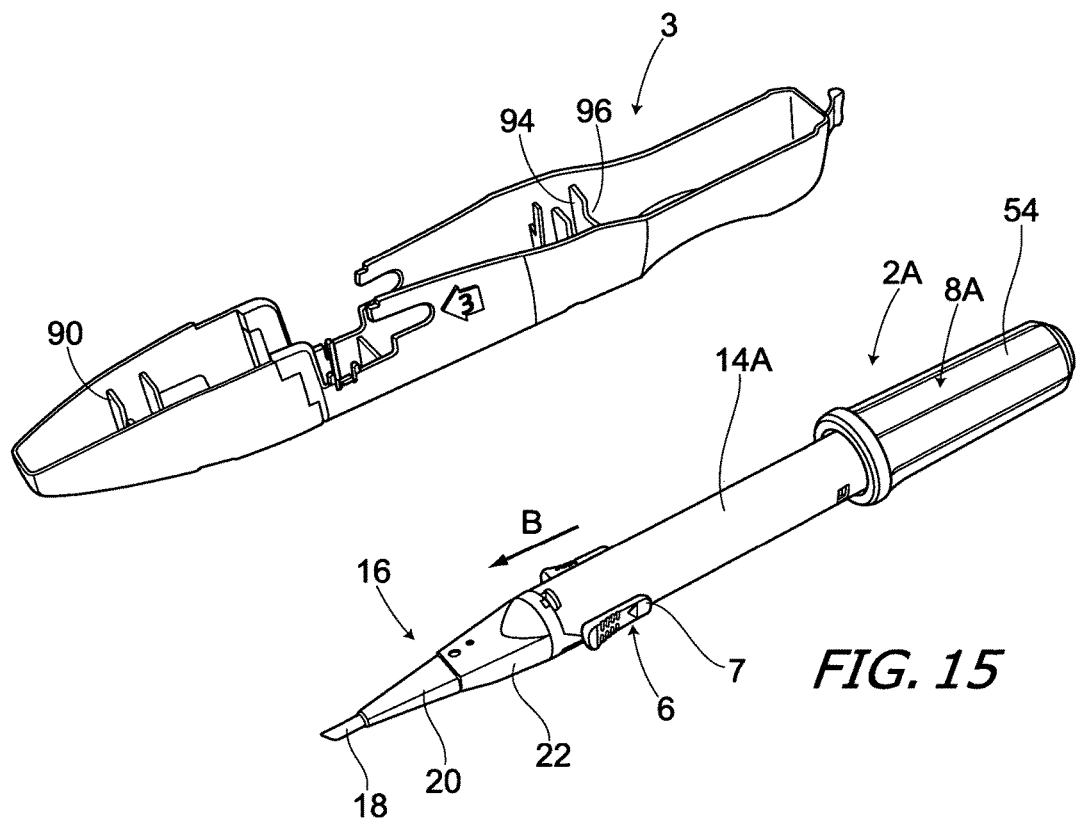
FIG. 15 is a perspective view showing another aspect of the operation of the exemplary IOL insertion system illustrated in FIG. 1.

It should also be noted here that the front portion 62 of the exemplary case 3 may include one or more support walls 90 (two in the exemplary embodiment) with slots 92 in which the insertion tube 16 is supported (FIG. 10). The width of each slot 92 (in a direction perpendicular to the lens advancement axis A) is equal to the width of the portion of the insertion tube 16 that is located therein. Similarly, the rear portion 64 includes a wall 94 (FIG. 15) with a slot 96 that is smaller in width than, and located distally of, the distal end of the handle 54. As a result, the IOL insertion apparatus main body 14A, insertion tube 16 and handle 54 may not be moved forward (i.e., in the direction of arrow B in FIG. 12) when the insertion apparatus 2A is located within the case 3. Also, as discussed above, the insertion apparatus 2A may not be pulled out of the case 3 (i.e., in the direction of arrow A in FIGS. 12 and 13) when the slider grips 7 are within the storage slots 66.

Figure 11:
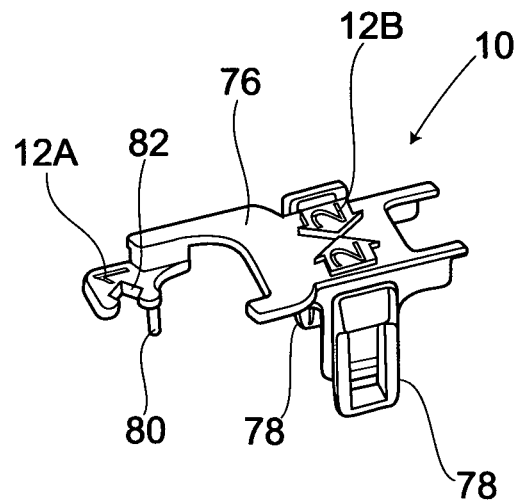
FIG. 11 is a perspective view of the exemplary cover illustrated in FIG. 1.

The exemplary cover 10, which is shown in detail in FIG. 11, includes a flat main body 76 and a pair of clips (or other attachment devices) 78. The clips 78 are size and positioned such that they can be located in the removal slots 68, and are configured to interlock with the engagement members 70 on the case 3. The clips 78, which extend downwardly from and are perpendicular to the main body 76, are resiliently deflectable about the main body at the point at which the clips are attached to the main body. As a result, the cover 10 can be easily secured to and removed from the case 3 by pressing the top ends of the clips 78 toward one another.

A protrusion 80 (FIG. 10), which extends downwardly from the bottom surface of the main body 76, is located such that it will extend into the first insertion hole 26 on the insertion tube 16 when the IOL insertion apparatus 2A is located within the case 3 and the cover 10 is secured to the case. The protrusion 80 is located within the path of the IOL adjacent to the distal end of the IOL optic 42 and, therefore, prevents distal movement of the IOL 40 within the lens placement section 28 during shipping and other times prior to use. The protrusion 80 is removed from the IOL path when the cover 10 is removed from the case 3. The cover 10 also includes an injection port opening 82 that will be aligned with insertion tube injection port 24 when the IOL insertion apparatus 2A is located within the case 3 and the cover 10 is secured to the case.

The cover 10 may be attached to the case 3, with each of the clips 78 located with a portion of a removal slot 68 and secured to an engagement member 70, when the lock mechanism 4 is in the locked state illustrated in FIG. 1. The clips 78 are also positioned forward of the slider grips 7, thereby preventing the slider 6 from being moved forwardly to unlock the lock mechanism 4 and move the IOL 40, when the cover 10 is secured to the case 3.

IV. ASSEMBLY

The exemplary IOL insertion system 1 may be assembled from an IOL insertion apparatus 2A and case 3 in a variety of ways. One exemplary assembly methods begins with an IOL insertion apparatus 2A that is complete, but for the loading of the IOL 40 and the attachment of the insertion tube 16 to the main body 14A, and the front and rear portions 62 and 64 of the case 3 separated from one another. In the initial step of the exemplary assembly method, the slider 6 and plunger 8 are attached to the main body 14A and the slider 6 is moved to its forward position so that the grip will be located within the removal slots 68. The main body 14A is then attached to the rear portion 64 of the case 3, which is still separated from the front portion 62, and the slider 6 is moved to the rearward position with the grips 7 within the storage slots 66. The IOL 40 is then placed in the lens placement section 28, with the outer edge of the optic 42 on the rails 38, and the supports 44 and 46 located distally and proximally of the optic. The inward protrusions 48 (FIG. 5) prevent the IOL 40 from moving in the rearward direction. The insertion tube 16 may then be attached to the front end of the main body 14A such that the lens placement section 28 is covered by the protector 22.

Next, the cover 10 is inserted onto the case 3. The clips 78 move through the removal slots 68 until they clip onto the engagement members 70, thereby securing the cover 10 to the case 3. The cover protrusion 80 will now extend through the first insertion hole 26 and be positioned between the forward support 44 and the optic 42 of the IOL 40. As a result, movement of the IOL 40 is held between the lens placement section inward protrusions 48 and the cover protrusion 80 with no physical load is applied thereto (FIG. 10). The proximal end of the case front portion 62 is then attached to the distal end of the rear portion 64 from underneath, thereby completing assembly of the exemplary IOL insertion system 1 (FIG. 1).

V. OPERATION AND INSTRUCTIVE INDICIA

Operation of the exemplary IOL insertion system 1 is discussed below with reference to FIGS. 1 and 12-16. The operational method may includes a number of step that are intended to be performed in a particular order. Some of the steps are associated with unlocking the lock mechanism 4 and removing the IOL insertion apparatus 2A from the case 3, some of the steps are associated with the operation of the IOL insertion apparatus itself, and at least one step is associated with both.

The exemplary IOL insertion system 1 may be provided with indicia that guides the operator through the initial steps in the proper sequence. More specifically, the exemplary IOL insertion system 1 includes markers 12A-12C. Each marker includes a number and, where appropriate, a directional indicator. Marker 12A is a "1" and is located on the cover 10 adjacent to the opening 82 for the injection port 24. Marker 12B, which is located on the cover 10 near the clips 78, includes a pair of inwardly facing arrows and each arrow has a "2" associated therewith. Marker 12C may be located on one or both sides of the case 3 adjacent to one or both of the storage slots 66. In the illustrated implementation, marker 12C consists of a forwardly facing arrow and a "3" adjacent to each of the storage slots 66 and, accordingly, each of the slider grips 7 when the IOL insertion system 1 is in its initial, pre-use state. As will be apparent from the discussion below, the markers 12A-12C reduce the likelihood of operator error by guiding the operator through the associated steps in the correct sequence.

The exemplary IOL insertion system 1 may be operated as follows. The IOL insertion system may be provided to the operator in a sterile bag and removed therefrom while holding the handle 72 (FIG. 1). A volume of viscoelastic material sufficient to fill the region around the IOL 40 may then be injected into the insertion tube 16 by way of injection port 24 (note marker 12A). The ends of the cover clips 78 adjacent to the main body 76 may then be pressed together (note marker 12B) to pivot the clips away from the engagement members 70, thereby disconnecting the cover 10 from the case 3. The cover 10 may then be removed from the case 3, as shown in FIG. 12. After the cover 10 has been removed from the case 3, the clips 78 will no longer prevent the slider grips 7 from being moved forwardly and the protrusion 80 will no longer prevent the IOL 40 from being moved forwardly. The lock mechanism 4 will, however, still be in the locked state.

As illustrated in FIG. 13, the next step is to move the slider 6 in the forward direction (note marker 12C) until the slider grips 7 have moved out of the storage slots 66 and, in the illustrated embodiment, have come into contact with a front ends of the removal slots 68. Such movement of the slider 6 causes the IOL 40 to move from the lens placement section 28 to the transition section 20, thereby causing the lateral sides of IOL optic 42 to fold upwardly as the lens holder 11 pushes the central portion of the IOL optic downwardly (FIG. 14). As the IOL 40 moves forwardly into the transition section 20, the protrusion 74 bends the distal IOL support 44 such that the free end of the support is positioned on the upper surface of the folded IOL optic 42 (FIG. 14). In particular, the slanted rearwardly facing surface of the protrusion 74 (FIG. 10) scoops up the distal IOL support 44 as it is bent, thereby facilitating reliable positioning of the distal IOL support on the upper surface of the folded IOL optic 42. The lens contact surface 5 of the slider 6 also scoops up the proximal IOL support 46 and pushes it forwardly such that the proximal IOL support 46 will also be positioned on the upper surface of the folded IOL optic 42. With respect to the folding of the IOL optic 42, the distal portion is folded to a greater extent than the proximal portion, with the lateral edges folded up and the center pushed down, due to the tapered shape of the interior of the transition section 20. This completes the initial folding of the IOL 40.

Movement of the slider 6 from the position illustrated in FIG. 12 to the position illustrated in FIGS. 13 and 14 also unlocks the lock mechanism 4 because the slider grips 7 are no longer within the storage slots 66 and, instead, are within the removal slots 68. The IOL insertion apparatus 2A may now be removed from the case 3 by simply lifting the apparatus in the direction identified by arrow A in FIG. 13. In addition to freeing up the IOL insertion apparatus 2A for use by the operator, removal of the IOL insertion apparatus from the case 3 also removes the protrusion 74, which is part of the case and which facilitated reliable folding of the IOL 40 during movement of the slider 6, from the path of the IOL. Thus, the protrusion 74 is located within the path of the IOL 40 when needed (i.e. during the initial folding of the IOL) and is automatically removed from the path when appropriate (i.e. prior to operation of the plunder 8A).

Figure 16:
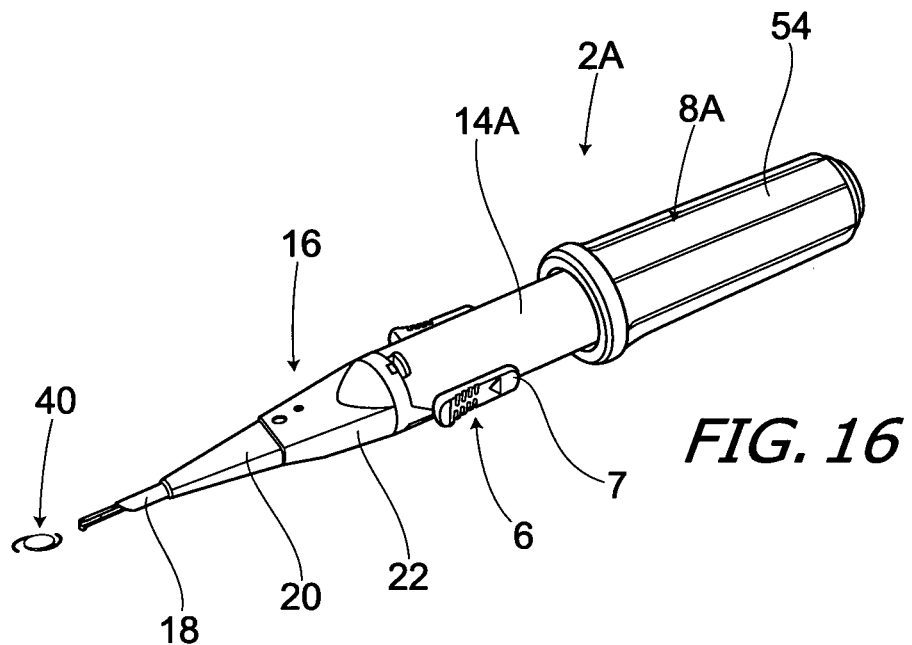
FIG. 16 is a perspective view showing another aspect of the operation of the exemplary IOL insertion system illustrated in FIG. 1.

Next, the operator pushes the plunger handle 54 forward in the direction of arrow B (FIG. 15) until the threads associated with the inner surface of the handle engage the thread (note protrusion 32 in FIG. 5) on the main body 14A. The handle 54 may then be rotated to drive the plunger 8A. Forward movement of the plunger rod 51 drives the IOL 40 into, and then through, the nozzle 18 and then into the eye (FIG. 16). The IOL 40 is further folded from the state illustrated in FIGS. 14 and 15 as it moves into the nozzle 18. The above-described initial state of the folded IOL 40, i.e. the IOL optic 42 folded with the supports 44 and 46 resting on the upper surface thereof, facilitates the subsequent folding associated with movement of the plunger rod 51.

It should be again emphasized here that the IOL insertion apparatus 2A is secured to the case 3 by the lock mechanism 4 until the slider 6 has been moved forward, thereby unlocking the lock mechanism so that the IOL insertion apparatus can be removed from the case. By incorporating such movement of the slider 6 into the unlocking process, the present IOL insertion system 1 prevents the operator from erroneously pushing the IOL 40 with the plunger 8A until after the IOL has undergone the initial folding associated with the slider 6.

VI. OTHER EXEMPLARY EMBODIMENTS

The present inventions are not limited to the exemplary embodiments described above.

Figure 17:
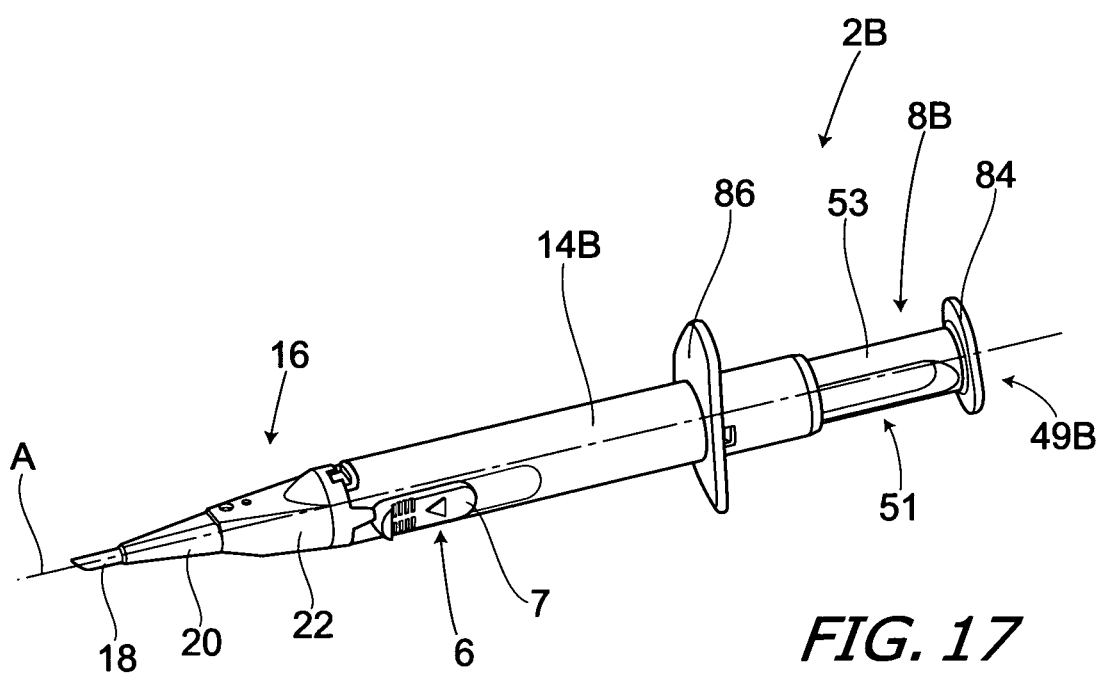
FIG. 17 is a perspective view of another exemplary IOL insertion apparatus that may be combined with a case in the manner illustrated in FIG. 1 to form an IOL insertion system.

For example, in addition to screw-type IOL insertion apparatus such as that described above, the present inventions are applicable to push-type IOL insertion apparatus. One example of such a push-type IOL insertion apparatus is generally represented by reference numeral 2B in FIG. 17. The push-type IOL insertion apparatus 2B is essentially identical to apparatus 2A and similar elements are represented by similar reference numerals. Here, however, instead of a screw-type operational member, the plunger 8B includes a push-type operational member 49B that operates in a manner similar to a syringe. Operational member 49B includes a disk-shaped member 84 on the proximal end of the proximal rod portion 53, and a flange 86 on the outer surface of the main body 14B. The plunger rod 51 is driven by resting one or more fingers on the flange 86 and pushing the disk-shaped member 84 with the thumb. The IOL insertion apparatus 2B may be combined, for example, with the case 3 and cover 10 described above to form an IOL insertion system that requires operation of the slider 6 prior to removal of the IOL insertion apparatus from the case.

Another exemplary IOL insertion system, which is generally represented by reference numeral 1C in FIG. 18, includes an IOL insertion apparatus 2C and a case 3C. IOL insertion system 1C is essentially identical to system 1 and similar elements are represented by similar reference numbers. For example, IOL insertion system 1C includes a screw-type IOL insertion apparatus 2C, a case 3C, a lock mechanism 4 and a cover 10C. In the interest of brevity, the discussion below focuses on the differences between the two systems.

As illustrated in FIG. 18, the exemplary cover 10C includes clips 78C that extend above the main body 76 to a greater extent than do the clips 78 of the cover 10. The additional length makes the clips 78C easier to grip and the cover 10C easier to remove.

Turning to FIGS. 19 and 20, in the exemplary IOL insertion apparatus 2C, the location of the injection port 24C on the insertion tube 16C decreases the likelihood that the cannula (not shown) delivering the viscoelastic material will come into contact with the IOL 40. Additionally, the cover 10C is provided with a frustoconical injection port opening 82C that will be aligned with insertion tube injection port 24C when the IOL insertion apparatus 2C is located within the case 3C and the cover is secured to the case. The frustoconical injection port opening 82C guides the cannula into the injection port 24C.

Referring to FIG. 21, the exemplary IOL insertion apparatus 2C includes a lens placement section 28C with a pair of lens covers 29 that extend over the inward protrusions 48 (FIG. 5) and portions of the IOL optic 42 and proximal support 46. The lens covers 29 prevent upward movement of the IOL 40 prior to operation of the slider 6C (e.g., during shipping or handling by the operator). As such, the lens covers 29 increase the likelihood that the IOL 40 will be properly positioned when the operator pushes the slider 6C forward. Additionally, as shown in FIG. 22, the lens placement section 28C has a bottom surface 34C with a groove 35 that guides the plunger rod 51C (FIG. 24) as it passes through the lens placement section, thereby increasing the likelihood that the plunder rod 51 will remain properly oriented.

With respect to the exemplary slider 6C, and turning to FIG. 23, the slider has a pivotable lens holder 11C with a pair of protrusions 13C. The dual protrusion arrangement causes the cause the lens holder 11C to engage the inner surface of the insertion tube 16C, and begin the pivoting and associated IOL folding, at an earlier point in the movement of the slider 6C than would be the case with the single protrusion embodiment illustrate in FIG. 14. Such earlier folding of the IOL 40 helps insure that the edge of the IOL is positioned in the manner illustrated in FIG. 14 so that the proximal IOL support 46 can slide over the IOL optic 42. With respect to deflection of the proximal IOL support 46, the exemplary slider 6C includes a lens contact assembly 5C that has a support post 5C-1 and a vertical guide surface 5C-2 that tapers outwardly in the proximal to distal direction. The lens contact assembly 5C insures that the proximal IOL support 46 will deflect in the manner described above with reference to FIG. 14.

Figure 24:
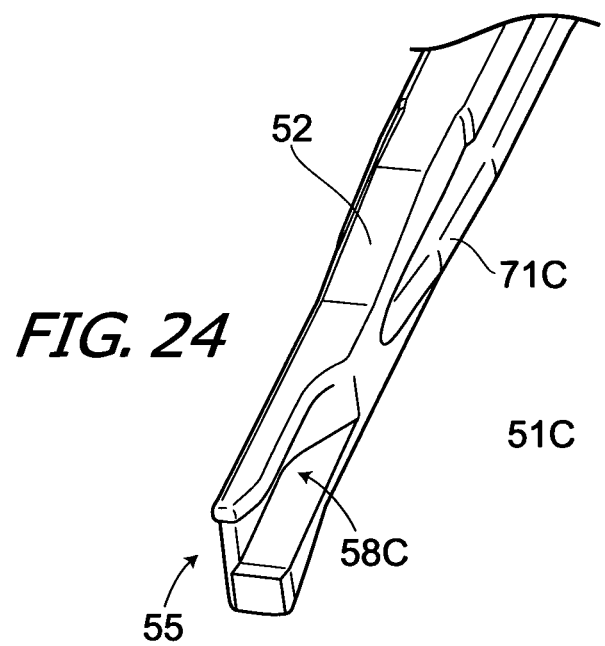
FIG. 24 is a perspective view of a portion of the plunger rod of the exemplary IOL insertion apparatus illustrated in FIG. 18.

As illustrated example in FIG. 24, the exemplary plunger rod 51C has a rib 71C that extends distally to a point adjacent to the recess 58C. The rib 71C increases the rigidity of plunger rod 51C which, in turn, helps to maintain the alignment of the plunger rod 51C. The shape of the recess 58C, which is larger than recess 58, helps insure that the proximal support 46 will move out of the recess once in the eye.

Figure 25:
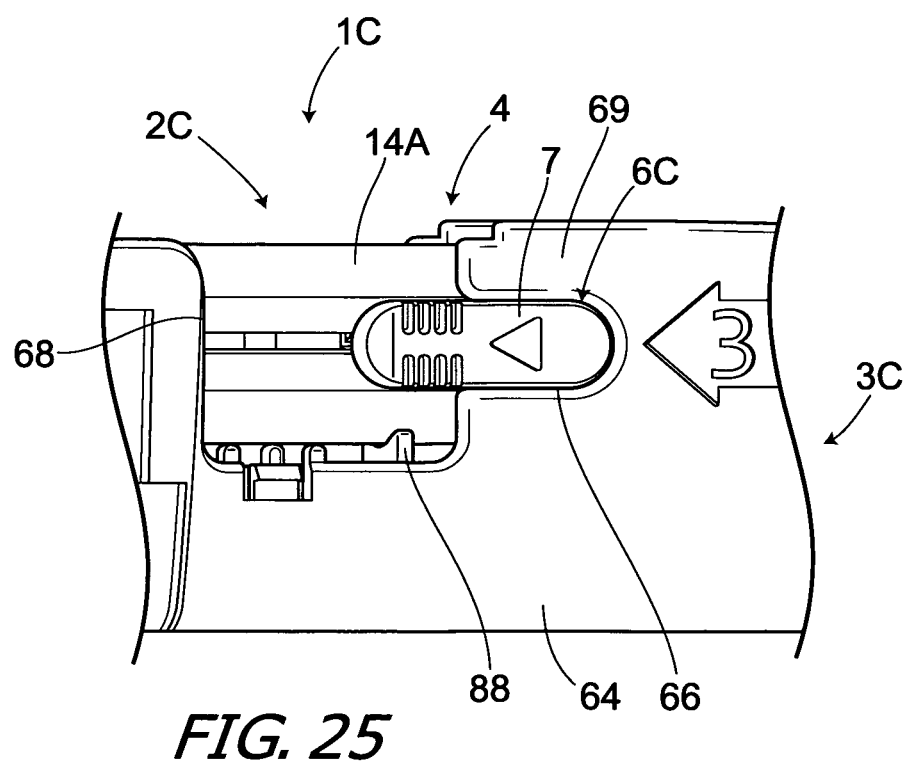
FIG. 25 is a side view of a portion of the exemplary IOL insertion apparatus illustrated in FIG. 18.

Referring to FIG. 25, the exemplary case 3C includes a support member 88 that engages the bottom of the main body 14A when the IOL insertion apparatus 2C is stored within the case and the lock mechanism 4 is in the locked state (as shown). The support member 88, which may be a thin wall with a curved upper surface, prevents the main body 14A from bending in the downward direction as the user is pushing the slider 6C forwardly. Such bending could result in an undesirable level of friction between the case 3C and the slider grip 7.

Figure 26:
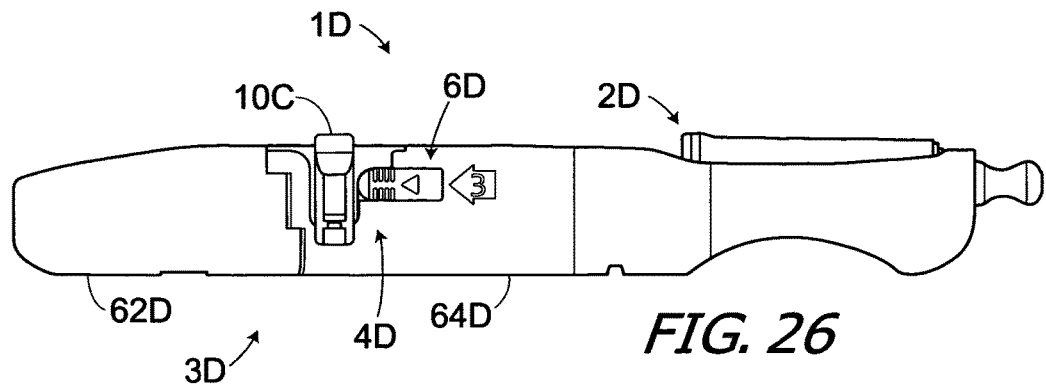
FIG. 26 is a perspective view of an IOL insertion system, including an IOL insertion apparatus and an insertion apparatus case, in accordance with one embodiment of a present invention.

Another exemplary IOL insertion system, which is generally represented by reference numeral 1D in FIG. 26, includes an IOL insertion apparatus 2D and a case 3D. IOL insertion system 1D is essentially identical to system 1C and similar elements are represented by similar reference numbers. For example, IOL insertion system 1D includes a screw-type IOL insertion apparatus 2D, a lock mechanism 4D, and a cover 10C. In the interest of brevity, the discussion below focuses on the differences between the two systems.

Figure 27:
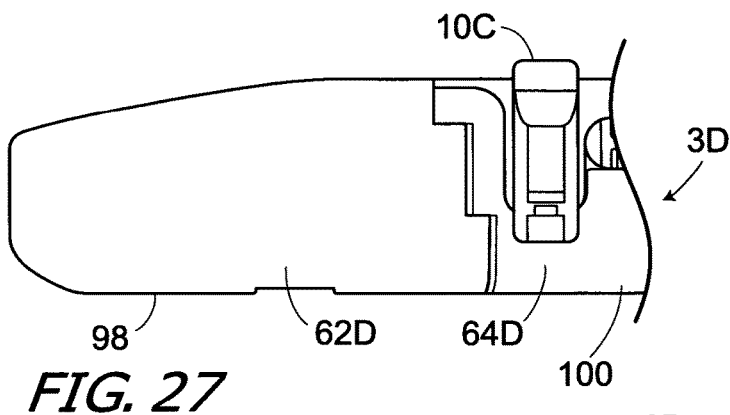
FIG. 27 is a side view of a portion of the exemplary IOL insertion system illustrated in FIG. 26.

The present inventor has determined that there may be some instances where, during the first step of the two-step process, the operator will place the case on a table or other flat support surface, hold the front portion of the case with one hand and the push the slider forward the other hand. Referring first to the embodiment illustrated in FIG. 18, the front portion 62 of the case 6C includes a bottom surface that tapers upwardly. If the operator pushes the front portion 62 of the case 3C downwardly with too much force while firmly holding the slider grips 7, the front portion of the case may deflect, the case protrusion 74 may be completely or partially pulled out of the IOL path, and the IOL distal support 44 may not deflect properly. The front portion 62D of the exemplary case 3D illustrated in FIGS. 26 and 27 includes a flat bottom surface 98, which is aligned with the flat bottom surface 100 of the rear portion 64D, that prevents such bending.

Figure 28:
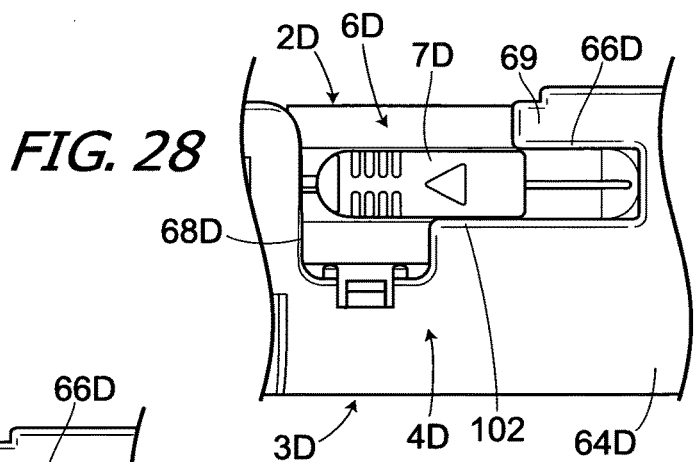
FIG. 28 is a side view of a portion of the exemplary IOL insertion system illustrated in FIG. 26.
Figure 29:
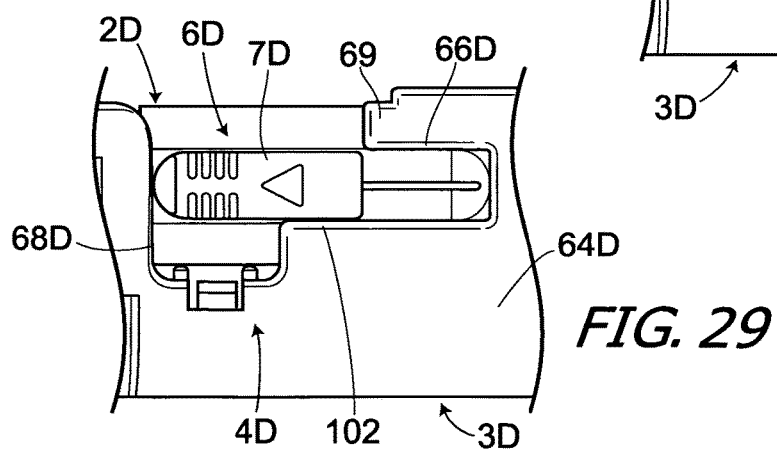
FIG. 29 is a side view of a portion of the exemplary IOL insertion system illustrated in FIG. 26.

The present inventor has also determined that there may be some instances where the operator attempts to pull the insertion apparatus out of the case, in a direction that is slightly angled from vertical, before the slider movement has been completed and the slider has engaged the distal wall of the removal slot. The curvature of the proximal ends of the slider grips may create a gap, between the curved proximal ends and the distal end of the storage slot protrusion (note grip 7 and protrusion 69 in FIG. 25) that invites these attempts. Turning to FIG. 28, the respective shapes of the slider grip 7D (not the flat proximal end), storage slot 66D and removal slot 68D (note extension 102) prevent the insertion apparatus 2D from being pulled out of the case 3D when the slider 6D is only in the almost fully forward position illustrated in FIG. 28. The top corner of the slider grip 7D is in contact with the bottom corner of the protrusion 69. Only after the slider 6D is moved to the fully forward position illustrated in FIG. 29 will removal of the insertion apparatus 2D from the case 3D be possible.

Numerous other modifications and/or additions to the above-described preferred embodiments would be readily apparent to one skilled in the art. It is intended that the scope of the present inventions extends to all such modifications and/or additions.

We claim:

1. An ocular implant insertion apparatus, comprising:
    a main body configured to store an ocular implant, with an optic and haptics, such that one of the haptics is a proximal haptic and one of the haptics is a distal haptic;
    a nozzle associated with the main body; and
    a plunger, carried within the main body and movable along a lens advancement axis, including a rod having a proximal portion and a distal portion, the proximal portion of the rod including an operational member, and the distal portion of the rod including a lens contact portion and a recess for the proximal haptic that is above the lens contact portion and that extends proximally from the lens contact portion, the recess having an first lateral side that is open, a second lateral side that is closed by a lateral wall, and an open distal end.

2. An ocular implant insertion apparatus as claimed in claim 1, wherein
    the plunger includes a top wall that extends over at least a portion of the recess.

3. An ocular implant insertion apparatus as claimed in claim 1, wherein
    the plunger includes a slanted wall that defines the proximal end of the recess.

4. An ocular implant insertion apparatus as claimed in claim 3, wherein
    the slanted wall is oriented at a non-perpendicular angle with respect to the lens advancement axis.

5. An ocular implant insertion apparatus as claimed in claim 3, wherein
    the slanted wall extends from the lateral wall to the first lateral side that is open.

6. An ocular implant insertion system as claimed in claim 1, further comprising:
    a slider movable relative to the plunger from a pre-use slider position to a second slider position.

7. An ocular implant insertion apparatus as claimed in claim 6, wherein
    the proximal haptic includes a free end; and
    movement of the slider from the pre-use slider position to the second slider position moves the free end of the proximal haptic over the optic.

8. An ocular implant insertion apparatus as claimed in claim 6, wherein
    the distal haptic includes a free end; and
    movement of the slider from the pre-use slider position to the second slider position moves the free end of the distal haptic over the optic.

9. An ocular implant insertion apparatus as claimed in claim 1, wherein
    the operational portion comprises a rotatable handle.

10. An ocular implant insertion apparatus as claimed in claim 1, wherein
    the operational portion comprises a thumb rest.

11. An ocular implant insertion apparatus as claimed in claim 1, wherein
    the lens contact portion is planar.

* * * * *